(12) United States Patent
Paris et al.

(10) Patent No.: US 10,925,520 B2
(45) Date of Patent: Feb. 23, 2021

(54) DEVICES, SYSTEMS, AND METHODS FOR DETERMINING LINEAR AND ANGULAR ACCELERATIONS OF THE HEAD

(71) Applicant: University of Alaska Anchorage, Anchorage, AK (US)

(72) Inventors: Anthony J. Paris, Anchorage, AK (US); Jens Munk, Eagle River, AK (US)

(73) Assignee: UNIVERSITY OF ALASKA ANCHORAGE, Anchorage, AK (US)

( * ) Notice: Subject to any disclaimer, the term of this patent is extended or adjusted under 35 U.S.C. 154(b) by 246 days.

(21) Appl. No.: 16/017,434

(22) Filed: Jun. 25, 2018

(65) Prior Publication Data
US 2018/0303384 A1 Oct. 25, 2018

Related U.S. Application Data

(63) Continuation of application No. 14/144,791, filed on Dec. 31, 2013, now Pat. No. 10,028,679.

(60) Provisional application No. 61/747,411, filed on Dec. 31, 2012.

(51) Int. Cl.
*A61B 5/11* (2006.01)
*A61B 5/00* (2006.01)

(52) U.S. Cl.
CPC .......... *A61B 5/1126* (2013.01); *A61B 5/1121* (2013.01); *A61B 5/682* (2013.01); *A61B 5/6803* (2013.01); *A61B 5/6895* (2013.01)

(58) Field of Classification Search
CPC ..... A61B 5/1121; A61B 5/1126; A61B 5/682; A61B 5/6895
See application file for complete search history.

(56) References Cited

U.S. PATENT DOCUMENTS

| | | | |
|---|---|---|---|
| 6,941,952 B1 | 9/2005 | Rush, III | |
| 7,526,389 B2 | 4/2009 | Greenwald et al. | |
| 2004/0242976 A1 | 12/2004 | Abreu | |
| 2005/0203431 A1 | 9/2005 | Brodnick et al. | |
| 2009/0220921 A1 | 9/2009 | Abolfathi et al. | |
| 2011/0060237 A1 | 3/2011 | Kurosawa et al. | |
| 2011/0219852 A1 | 9/2011 | Kasten | |
| 2012/0143526 A1 | 6/2012 | Benzel et al. | |
| 2013/0211270 A1 | 8/2013 | St. Laurent et al. | |

(Continued)

OTHER PUBLICATIONS

Birmingham et al., (2013) "An Instrumented Mouthguard to Measure Head Accelerations due to Impact," Proceedings of the ASME 2013 Summer Bioengineering Conference, Jun. 26-29, Sunriver, OR, USA.

(Continued)

*Primary Examiner* — Christine H Matthews
(74) *Attorney, Agent, or Firm* — Ballard Spahr LLP

(57) ABSTRACT

Mouth guards and related systems and methods for determining linear and angular accelerations of the head of a subject. A plurality of accelerometers are operatively associated with the mouth guard and spaced from one another about the mouth guard. The accelerometers produce outputs indicative of the linear and angular acceleration of the mouth guard. Optionally, the mouth guard can be used in conjunction with a helmet that is provided with a plurality of accelerometers spaced about the helmet. In use, the outputs of the accelerometers of the helmet can be correlated to the outputs of the accelerometers of the mouth guard.

8 Claims, 24 Drawing Sheets

(56) References Cited

U.S. PATENT DOCUMENTS

2013/0245483 A1    9/2013   Eichler
2014/0187875 A1    7/2014   Paris et al.

OTHER PUBLICATIONS

Cernak, I. Animal Models of Head Trauma. NeuroRx. J Amer Soc Exper Neuro Ther. 2005; 2(3):410-22.
Kara et al., (2012) "Evaluation of an Instrumented Mouthguard to Measure the Accelerations of the Head due to Soccer Ball Heading," 12th Pan-American Congress of Applied Mechanics, Jan. 2-6, Port of Spain, Trinidad.
Paris et al., (2008) "Soccer Ball Heading Model," Proceedings of the ASME 2008 Summer Bioengineering Conference, Jun. 25-29, Marriott Resort, Marco Island, FL, USA.
Paris et al., (2010) "Accelerations of the Head During Soccer Ball Heading," Proceedings of the ASME 2010 Summer Bioengineering Conference, Jun. 16-19, Grand Beach Resort, Naples, FL, USA.
Roveti, Choosing a Humidity Sensor: a Review of Three Technologies. Humidity/Moisture (2001) (5 pages).
Non-Final Office Action dated Aug. 12, 2016 by the U.S. Patent and Trademark Office for U.S. Appl. No. 14/144,791, filed Dec. 31, 2013, and published as US 2014/0188010 on Jul. 3, 2014 (Inventor—Paris et al.; Applicant—University of Alaska Anchorage) (28 pages).
Non-Final Office Action dated Mar. 23, 2017 by the U.S. Patent and Trademark Office for U.S. Appl. No. 14/144,791, filed Dec. 31, 2013, and published as US 2014/0188010 on Jul. 3, 2014 (Inventor—Paris et al.; Applicant—University of Alaska Anchorage) (22 pages).
Final Office Action dated Nov. 30, 2017 by the U.S. Patent and Trademark Office for U.S. Appl. No. 14/144,791, filed Dec. 31, 2013, and published as US 2014/0188010 on Jul. 3, 2014 (Inventor—Paris et al.; Applicant—University of Alaska Anchorage) (24 pages).
Notice of Allowance dated Mar. 26, 2018 by the U.S. Patent and Trademark Office for U.S. Appl. No. 14/144,791, filed Dec. 31, 2013, and published as US 2014/0188010 on Jul. 3, 2014 (Inventor—Paris et al.; Applicant—University of Alaska Anchorage) (7 pages).
Issue Notification dated Jul. 4, 2018 by the U.S. Patent and Trademark Office for U.S. Appl. No. 14/144,791, filed Dec. 31, 2013, and published as US 2014/0188010 on Jul. 3, 2014 (Inventor—Paris et al.; Applicant—University of Alaska Anchorage) (1 page).
Non-Final Office Action dated Feb. 1, 2016 by the by the U.S. Patent and Trademark Office for U.S. Appl. No. 14/144,907, filed Dec. 31, 2013 and published as US 2014/0187875 on Jul. 3, 2014 (Inventor—Paris et al.; Applicant—University of Alaska Anchorage) (12 pages).
Final Office Action dated Nov. 16, 2016 by the by the U.S. Patent and Trademark Office for U.S. Appl. No. 14/144,907, filed Dec. 31, 2013 and published as US 2014/0187875 on Jul. 3, 2014 (Inventor—Paris et al.; Applicant—University of Alaska Anchorage) (15 pages).
Non-Final Office Action dated Jun. 7, 2017 by the by the U.S. Patent and Trademark Office for U.S. Appl. No. 14/144,907, filed Dec. 31, 2013 and published as US 2014/0187875 on Jul. 3, 2014 (Inventor—Paris et al.; Applicant—University. of Alaska Anchorage) (16 pages).
Notice of Allowance dated Jan. 5, 2018 by the by the U.S. Patent and Trademark Office for U.S. Appl. No. 14/144,907, filed Dec. 31, 2013 and published as US 2014/0187875 on Jul. 3, 2014 (Inventor—Paris et al.; Applicant—University. of Alaska Anchorage) (14 pages).
Issue Notification dated Apr. 11, 2018 by the by the U.S. Patent and Trademark Office for U.S. Appl. No. 14/144,907, filed Dec. 31, 2013 and published as US 2014/0187875 on Jul. 3, 2014 (Inventor—Paris et al.; Applicant—University. of Alaska Anchorage) (1 page).
Non-Final Office Action dated Oct. 5, 2018 by the U.S. Patent and Trademark Office for U.S. Appl. No. 15/965,185, filed Apr. 27, 2018 and published as US 2018/0242911 on Aug. 30, 2018 (Inventor—Paris et al.; Applicant—University of Alaska Anchorage) (17 pages).
Response to Non-Final Office Action filed on Jan. 7, 2019 with the U.S. Patent and Trademark Office for U.S. Appl. No. 15/965,185, filed Apr. 27, 2018 and published as US 2018/0242911 on Aug. 30, 2018 (Inventor—Paris et al.; Applicant—University of Alaska Anchorage) (11 pages).
Notice of Allowance dated Apr. 5, 2019 by U.S. Patent and Trademark Office for U.S. Appl. No. 15/965,185, filed Apr. 27, 2018 and published as US 2018/0242911 on Aug. 30, 2018 (Inventor—Paris et al.; Applicant—University of Alaska Anchorage) (8 pages).
U.S. Appl. No. 61/747,411, filed Dec. 31, 2012, Anthony J. Paris (University of Alaska Anchorage).
U.S. Appl. No. 14/144,791 (U.S. Pat. No. 10,028,679), filed Dec. 31, 2012 (Jul. 24, 2018), Anthony J. Paris (University of Alaska Anchorage).
U.S. Appl. No. 61/827,996, filed May 28, 2013, Anthony J. Paris (University of Alaska Anchorage).
U.S. Appl. No. 14/144,907 (U.S. Pat. No. 9,955,918), filed Dec. 31, 2013 (May 1, 2018), Anthony J. Paris (University of Alaska Anchorage).
U.S. Appl. No. 15/965,185 (2018/0242911), filed Apr. 27, 2018 (Aug. 30, 2018), Anthony J. Paris (University of Alaska Anchorage).

DEVICES, SYSTEMS, AND METHODS FOR DETERMINING LINEAR AND ANGULAR ACCELERATIONS OF THE HEAD

CROSS-REFERENCE TO RELATED APPLICATIONS

This application is a continuation of U.S. patent application Ser. No. 14/144,791, filed Dec. 31, 2013, which claims the benefit of the filing date of U.S. Provisional Patent Application No. 61/747,411, filed Dec. 31, 2012. Each of these applications is incorporated herein by reference in its entirety.

FIELD

This application relates to devices, systems, and methods for measuring and/or determining the linear and angular acceleration experienced by the head of a subject in response to an impact force.

BACKGROUND

The human brain is susceptible to injury due to both linear and angular acceleration. Linear and angular acceleration above the threshold and/or other linear and angular acceleration characteristics, such as the time derivative of the acceleration (known as "the jerk"), that could cause brain injury can occur in athletes participating in sports, such as soccer, boxing, skiing, snowboarding, hockey, American football, motorcycle and automobile racing, and bicycling, and to soldiers who experience an explosive blast or other impact.

Accordingly, there is a need in the pertinent art for devices, systems, and methods for measuring both linear and angular acceleration of the head of a subject.

SUMMARY

Described herein is a mouth guard for determining the linear and angular acceleration of the head of a subject. The mouth guard can include a U-shaped element having an outer side wall, an inner side wall, and at least one biting surface. The outer side wall, the inner side wall, and the at least one biting surface can cooperate to define at least one channel configured to receive the upper teeth of the subject. The mouth guard can also include a plurality of accelerometers operatively associated with the U-shaped element. The plurality of accelerometers can be spaced from one another about the U-shaped element. Each accelerometer of the plurality of accelerometers can be configured to produce an output indicative of the linear and angular acceleration of the mouth guard.

The mouth guard can be provided as part of a system. Such a system can include processing circuitry positioned in operative communication with the plurality of accelerometers of the mouth guard. The processing circuitry can be configured to receive the outputs from the plurality of accelerometers of the mouth guard.

Also described herein is a helmet having a wall that defines an inner chamber. The inner chamber can be configured to receive the head of the subject. The helmet can include a plurality of accelerometers operatively associated with the wall of the helmet. The plurality of accelerometers can be spaced from one another about the helmet. Each accelerometer of the plurality of accelerometers of the helmet can be configured to produce an output indicative of the linear acceleration and angular acceleration of the helmet.

The helmet can also be provided as part of a system. Such a system can include processing circuitry positioned in operative communication with the plurality of accelerometers of the helmet. The processing circuitry can be configured to receive the outputs from the plurality of accelerometers. The processing circuitry can be further configured to convert the outputs from the plurality of accelerometers of the helmet into an output indicative of the linear and angular acceleration of the head of the subject.

In use, the head of the subject can be positioned within the helmet, and the mouth guard can be positioned in engagement with the upper teeth of the subject. In response to the delivery of a first impact force to the helmet, each accelerometer of the helmet can be configured to produce an output indicative of the linear and angular acceleration of the helmet, and each accelerometer of the mouth guard can be configured to produce an output indicative of the linear and angular acceleration of the mouth guard (which substantially corresponds to the linear and angular acceleration of the head of the subject). The outputs of the accelerometers of the helmet and the mouth guard can be transmitted to the processing circuitry. The processing circuitry can determine a transfer function configured to convert the outputs of the accelerometers of the helmet (linear and angular accelerations of the helmet) to the outputs of the accelerometers of the mouth guard (linear and angular accelerations of the mouth guard).

After the transfer function has been determined, the mouth guard can be disengaged from the teeth of the subject and removed from the mouth of the subject. Following removal of the mouth guard, a second impact force can be delivered to the helmet. In response to delivery of the second impact force, each accelerometer of the helmet can be configured to produce an output indicative of the linear and angular acceleration of the helmet. The outputs of the accelerometers of the helmet can then be transmitted to the processing circuitry. The processing circuitry can then apply the transfer function to the outputs of the accelerometers of the helmet to determine the linear and angular acceleration of the head of the subject.

BRIEF DESCRIPTION OF THE DRAWINGS

These and other features of the preferred embodiments of the invention will become more apparent in the detailed description in which reference is made to the appended drawings wherein:

In FIGS. 6-8, the x and y directions correspond with the chip x and y directions shown in FIG. 5A, where x is the head forward direction and y is the head upward direction.

In FIG. 10, the head coordinate system axes are denoted by x, y, and z, corresponding with the head front, left, and up directions and with the x, y, and z coordinate system origin at the head center of mass.

In FIGS. 15 and 16, the head coordinate system axes are denoted by x, y, and z, corresponding with the head front, left, and up directions and with the x, y, and z coordinate system origin at the head center of mass.

In FIG. 26, the head coordinate system axes are denoted by x, y, and z, corresponding with the head front, left, and up directions and with the x, y, and z coordinate system origin at the head center of mass.

In FIG. 27, the head coordinate system axes are denoted by x, y, and z, corresponding with the head front, left, and up directions and with the x, y, and z coordinate system origin at the head center of mass.

DETAILED DESCRIPTION

Figure 1A:
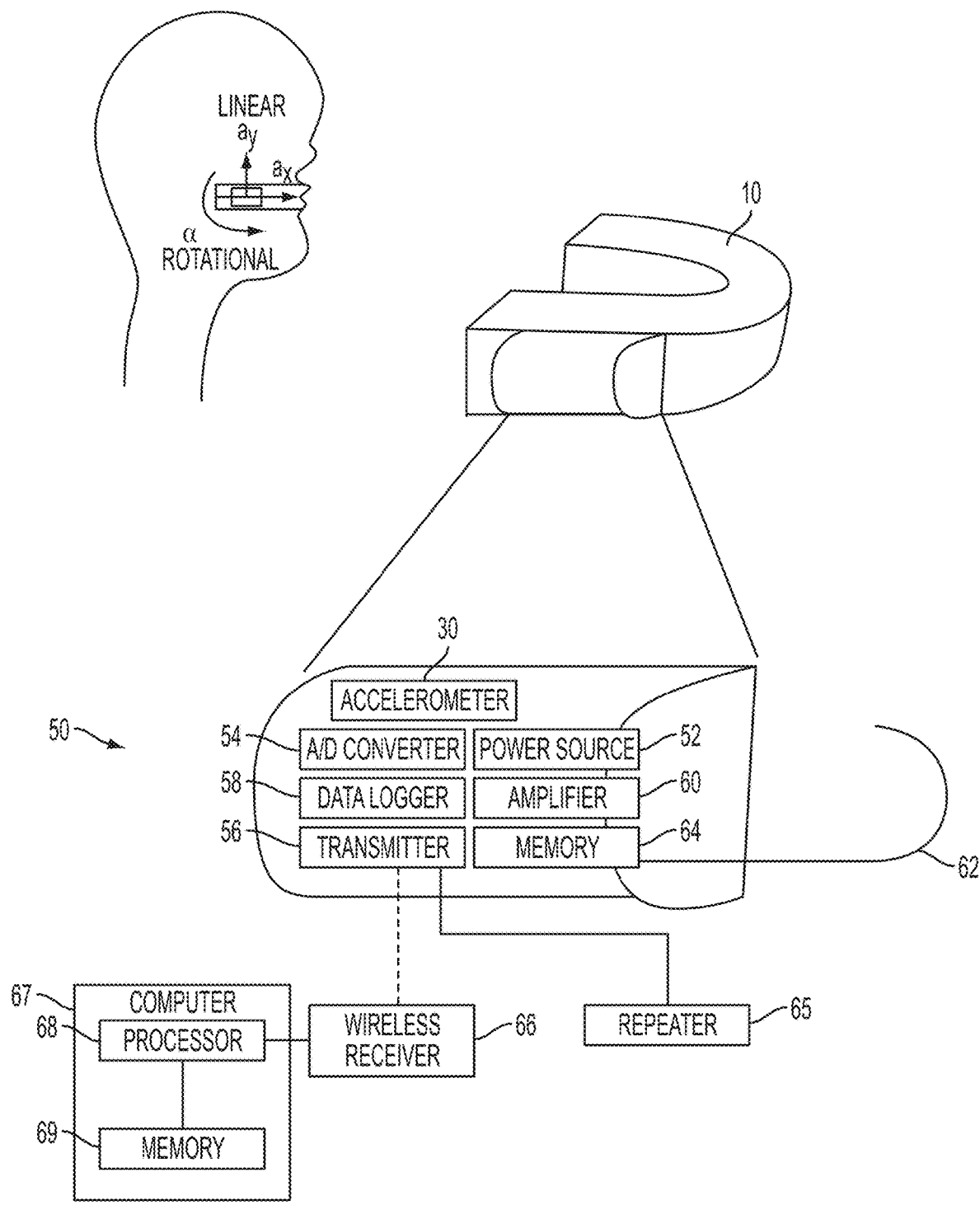
FIG. 1A is a schematic diagram of a measurement system comprising a mouth guard and processing circuitry as disclosed herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an accelerometer" can include two or more such accelerometers unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Described herein with reference to FIGS. 1-27 are devices, systems, and methods for determining the linear and angular acceleration of the head of a subject. It is contemplated that the subject can be a human or non-human subject. It is further contemplated that the subject can have a head, a mouth, and upper and lower teeth.

The Mouth Guard

Figure 1B:
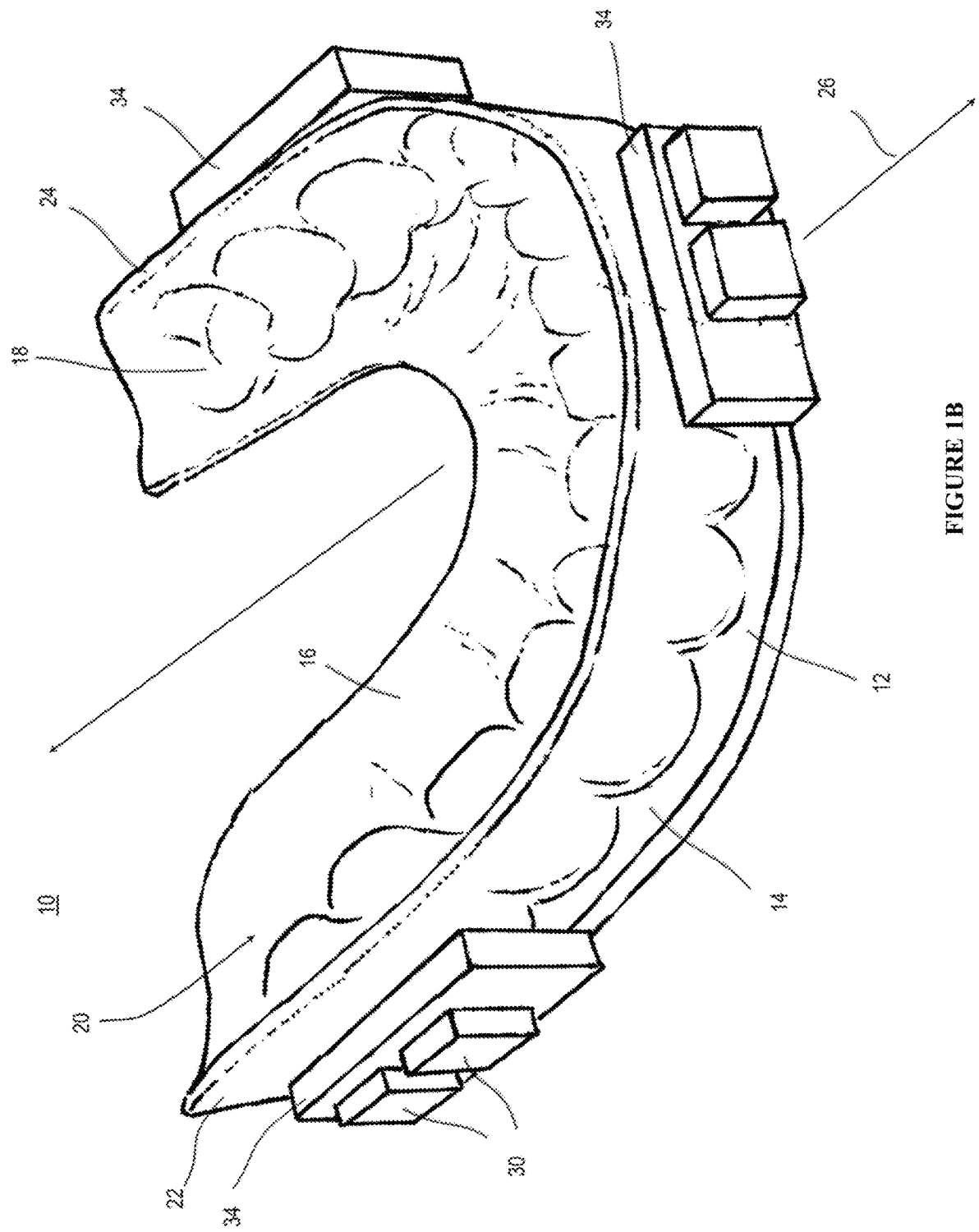
FIG. 1B is a perspective view of an exemplary mouth guard as disclosed herein.
Figure 1C:
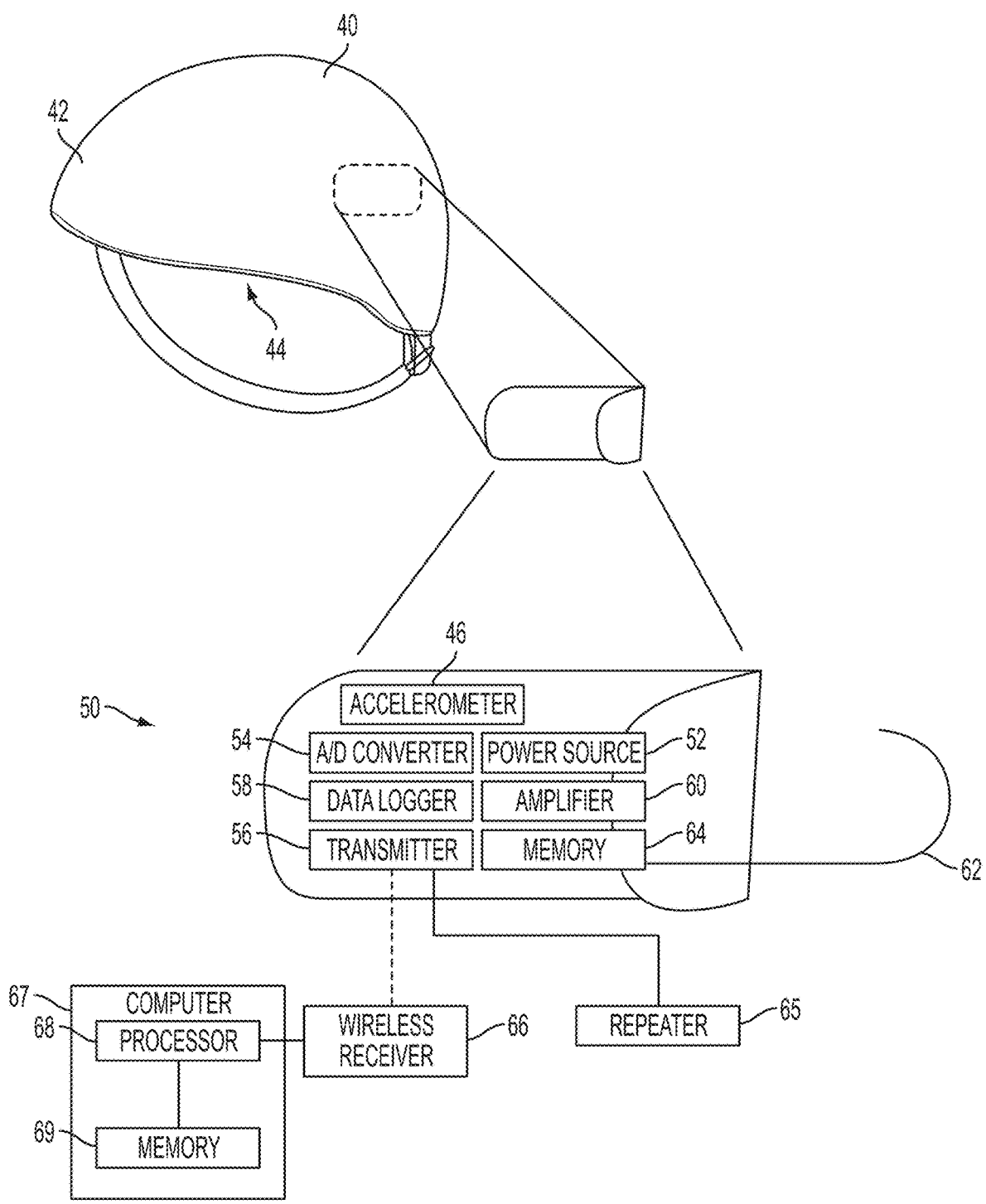
FIG. 1C is a schematic diagram of a measurement system comprising a helmet and processing circuitry as disclosed herein.

In exemplary aspects, and with reference to FIGS. 1A-1C, a mouth guard 10 can be provided for engagement with the teeth of the subject. In these aspects, it is contemplated that the mouth guard 10 can comprise a U-shaped element 12 having an outer side wall 14, an inner side wall 16, and at least one biting surface 18. It is further contemplated that the outer side wall 14, the inner side wall 16, and the at least one biting surface 18 can cooperate to define at least one channel 20 configured to receive the upper teeth of the subject. In exemplary aspects, the channel 20 can be shaped to conform to the upper teeth of the subject. In these aspects, the channel 20 can be formed from a mold of the upper teeth of the subject. It is contemplated that a good fit between the mouth guard 10 and the upper teeth and gums of the subject can create a vacuum seal that prevents the mouth guard from being loose and rattling against the teeth during head impacts. In use, it is contemplated that the mouth guard 10 can be tightly fitted to the upper teeth and gums and be configured for relatively loose engagement with the lower teeth of the subject.

In one aspect, the mouth guard 10 can comprise a plurality of accelerometers 30 operatively associated with the U-shaped element 12. In this aspect, it is contemplated that the plurality of accelerometers 30 can be spaced from one another about the U-shaped element 12. It is further contemplated that each accelerometer 30 of the plurality of accelerometers of the mouth guard 10 can be configured to produce an output indicative of the linear and angular acceleration of the mouth guard.

Figure 2:
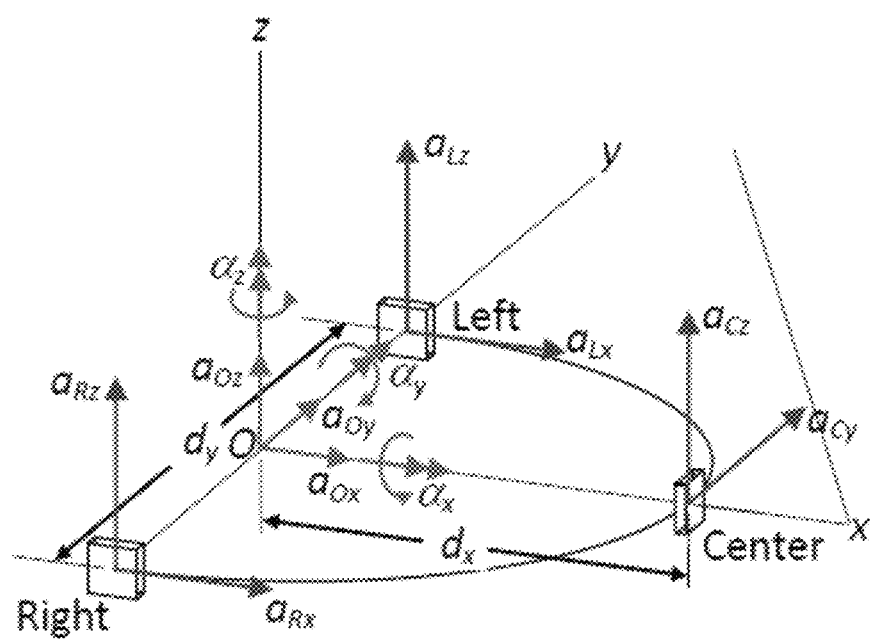
FIG. 2 depicts an exemplary local mouth guard coordinate system having axes x, y, and z and origin O. In the exemplary mouth guard system shown in FIG. 2, three 2-axis accelerometers (a total of six accelerometers to measure linear acceleration in the directions shown by the arrows originating from the respective accelerometers) are positioned and oriented in the mouth guard for accurate and precise determination of the angular and linear accelerations of the mouth guard origin O, marked by the arrows originating from point O.

In another aspect, the plurality of accelerometers 30 of the mouth guard 10 can optionally comprise nine single-axis accelerometers (capable of measuring linear acceleration in a single axis) positioned at three distinct locations about the U-shaped element 12, as shown in FIGS. 1B and 2. In this aspect, three orthogonal single-axis accelerometers can be positioned in a cluster at each of the three distinct locations. Alternatively, the plurality of accelerometers 30 of the mouth guard 10 can comprise three three-axis accelerometers (capable of measuring linear acceleration in three axes), with one accelerometer positioned at each of the three distinct locations. In exemplary aspects, when the plurality of accelerometers are positioned at three distinct locations and positioned and oriented within a common plane (for example and without limitation, within the xy plane) as shown in FIGS. 1B and 2, it is contemplated that the plurality of accelerometers can comprise three two-axis accelerometers, with one two-axis accelerometer positioned at each of the three distinct locations. In further exemplary aspects, when the plurality of accelerometers are positioned at three distinct locations and positioned and oriented within a common plane as shown in FIGS. 1B and 2, it is contemplated that the plurality of accelerometers can comprise six single-axis accelerometers, with a cluster of two single-axis accelerometers being positioned at each of the three distinct locations.

In exemplary aspects, the three distinct locations can correspond to first, second, and third locations spaced from one another about an arc defined by the U-shaped element 12. In these aspects, it is contemplated that the U-shaped element 12 can define opposed first and second ends 22, 24. It is further contemplated that the U-shaped element 12 can be substantially symmetrical about a central axis 26, which can optionally correspond to a y-axis as disclosed herein. In exemplary aspects, it is contemplated that the first location can be proximate the first end 22 of the U-shaped element 12, the second location can be proximate the second end 24 of the U-shaped element, and the central axis 26 can intersect the third location. Thus, it is contemplated that the three distinct locations at which the plurality of accelerometers are positioned can correspond to: (1) a position just outside the right molars of the subject; (2) a position just outside the left molars of the subject; and (3) a position just in front of the central incisors of the subject.

Although described herein as being positioned at three distinct locations within the mouth of the subject, it is contemplated that other positions and orientations of the plurality of accelerometers 30 can be employed to determine the linear and angular accelerations of the head of the subject. It is further contemplated that the plurality of accelerometers 30 can comprise any number of accelerometers that provide sufficient data to determine the linear and angular accelerations of the head of the subject. For example, it is contemplated that the plurality of accelerometers 30 can comprise more than nine accelerometers.

The majority of head impacts have a small duration (often a few thousandths of a second or less) and large angular accelerations. It is contemplated that, although gyroscopes are typically used to determine angular accelerations and velocities and positions, conventional gyroscopes cannot be used to measure many of the short-duration impacts that generate large angular accelerations of the head of the subject. Nonetheless, in appropriate conditions, it is contemplated that one or more gyroscopes can be used in place of one or more of the accelerometers of the plurality of accelerometers to determine the linear and angular accelerations of the head of the subject.

In exemplary aspects, the plurality of accelerometers 30 of the mouth guard can comprise microelectromechanical system (MEMS) accelerometers. In these aspects, it is contemplated that the MEMS accelerometers can be configured to measure large accelerations at relatively high acquisition rates while being small enough in mass to not significantly affect the inertia on the head of the subject. It is further contemplated that the MEMS accelerometers can be provided on a chip.

In other exemplary aspects, the disclosed mouth guard 10 can optionally comprise one or more hard thermoplastic materials. In these aspects, it is contemplated that the one or more hard thermoplastic materials can be heated and vacuum-formed to casts formed from impressions of the upper and/or lower jaws of the subject. In additional exemplary aspects, the disclosed mouth guard can optionally comprise one or more thermoset plastic materials, such as, for example and without limitation, acrylic materials. In these aspects, it is contemplated that the thermoset plastic materials can be molded to casts formed from impressions of the upper and lower jaws of the subject. In still other exemplary aspects, it is contemplated that the mouth guard can comprise one or more thermoplastic materials that can be softened in hot water and then placed in the mouth of the subject and fit to the upper teeth of the subject, as is conventionally known in the art. In these aspects, it is contemplated that the number of dental clinic visits and the amount of laboratory costs can be significantly reduced. It is further contemplated that the accelerometers 30 and processing circuitry 50 described herein can be configured to withstand temperatures far above the boiling point of water and can easily survive such a fitting.

Figure 22:
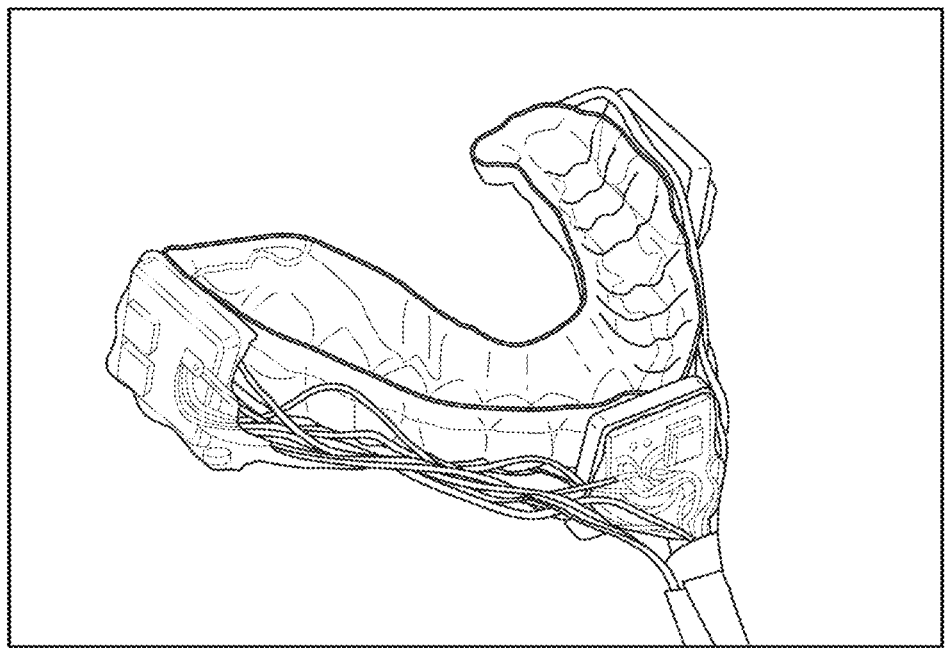
FIG. 22 displays an exemplary thermoplastic mouth guard with a bridge element, two PCB assemblies (each having two accelerometers), wiring, and sealant. A third PCB (having two accelerometers) is hidden from view on the left side of the mouth guard bridge element.

Optionally, in one aspect, the plurality of accelerometers 30 can be electrically coupled to a plurality of printed circuit board (PCB) assemblies. For example, in one exemplary aspect, and as shown in FIG. 22, the plurality of PCB assemblies can comprise three PCB assemblies spaced about the mouth guard 10 as disclosed herein with respect to the accelerometers 30. In this aspect, it is contemplated that when the plurality of accelerometers 30 comprises six accelerometers, each PCB assembly can be configured for electrical coupling to two accelerometers. Similarly, it is contemplated that when the plurality of accelerometers 30 comprises nine accelerometers, each PCB assembly can be configured for electrical coupling to three accelerometers. In exemplary aspects, it is contemplated that at least one PCB assembly can be securely received within a respective receptacle as further described herein.

Formation of the Mouth Guard

Figure 19A:
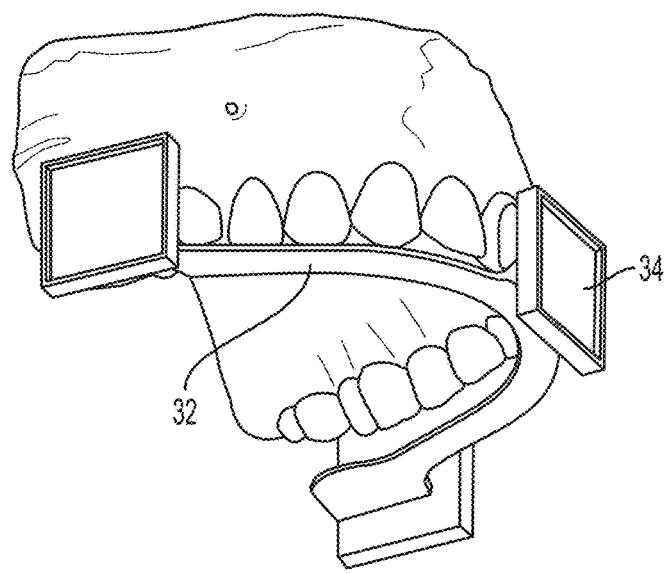
FIG. 19 shows the fitting of a bridge element to three-dimensional scans of the (A) upper jaw and (B) upper and lower jaws of a subject as disclosed herein.
Figure 19B:
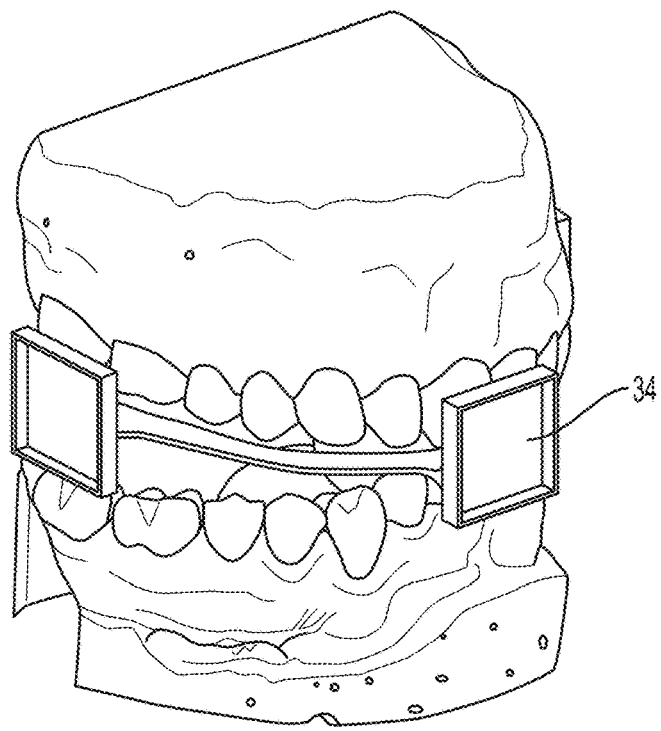
Figure 21:
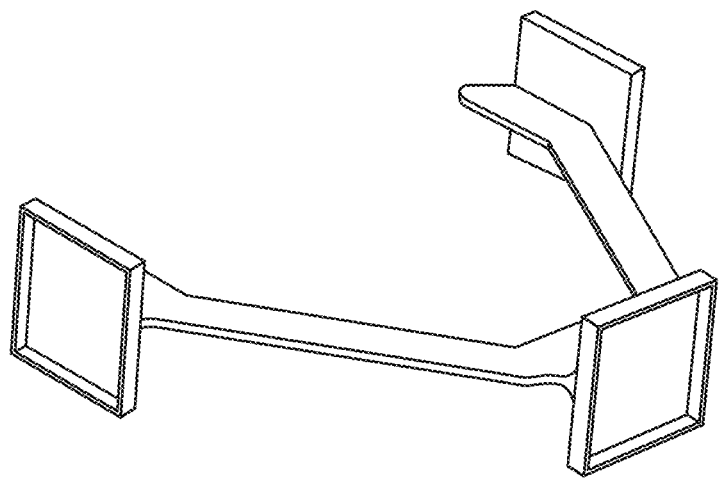
FIG. 21 displays an image of a bridge element printed using a three-dimensional printer.

In exemplary aspects, the mouth guard 10 can be formed from impressions of the teeth and gums of the upper and lower jaws of the subject. In these aspects, the impressions can be used to form a cast of the subject's teeth and gums using conventional methods. The casts of the teeth and gums of the subject can then be scanned using a three-dimensional (3-D) scanner. Alternatively, in other exemplary aspects, an intraoral 3-D dental scan of at least the teeth, gums, and soft and hard palate of the upper and lower jaws of the subject can be performed. It is contemplated that the solid models formed from the scans can be printed in 3-D to form a cast comprising a plastic material, such as, for example and without limitation, Acrylonitrile Butadiene Styrene (ABS). It is further contemplated that the 3-D scans of the casts can then be uploaded to a 3-D solid modeling software package. As shown in FIGS. 19A and 19B, a bridge element 32 can be fitted to the scans. It is contemplated that the bridge element 32 can be configured to fit to the upper jaw such that there is about 2 mm of clearance between the bridge and the teeth and gums of the subject. It is further contemplated that a 2 mm thick acrylic thermoplastic sheet can be vacuum-formed to the cast of the teeth and gums of the upper jaw of the subject and trimmed to form the mouth guard. Clearance can be confirmed between the bridge 32 and the lower jaw, and the bridge 32 can be adjusted as necessary. As depicted in FIG. 21, it is contemplated that the bridge 32 can be constructed of ABS or other plastic material using a 3-D printer as is known in the art. It is further contemplated that the bridge 32 can be affixed to the mouth guard 10 using medical-grade adhesive. In exemplary aspects, it is contemplated that a second soft layer of thermoplastic material can be heated and vacuum-formed over and bonded to the mouth guard 10, the bridge element 32, and at least a portion of the processing circuitry 50. In these aspects, it is contemplated that the second layer of thermoplastic material can substantially encapsulate and seal at least a portion of the processing circuitry 50 and thereby protect the processing circuitry. It is further contemplated that the second layer of thermoplastic material can be shaped to make the mouth guard 10 more ergonomic.

Figure 20:
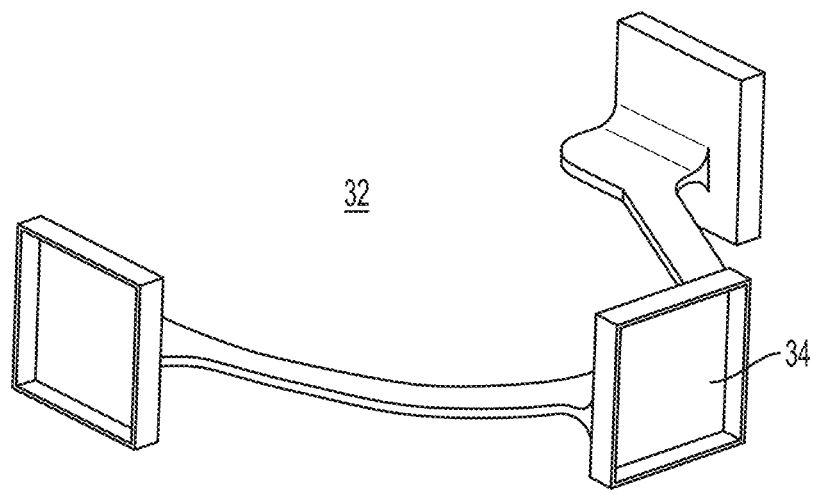
FIG. 20 depicts a solid model of a fitted bridge element as disclosed herein.
Figure 23:
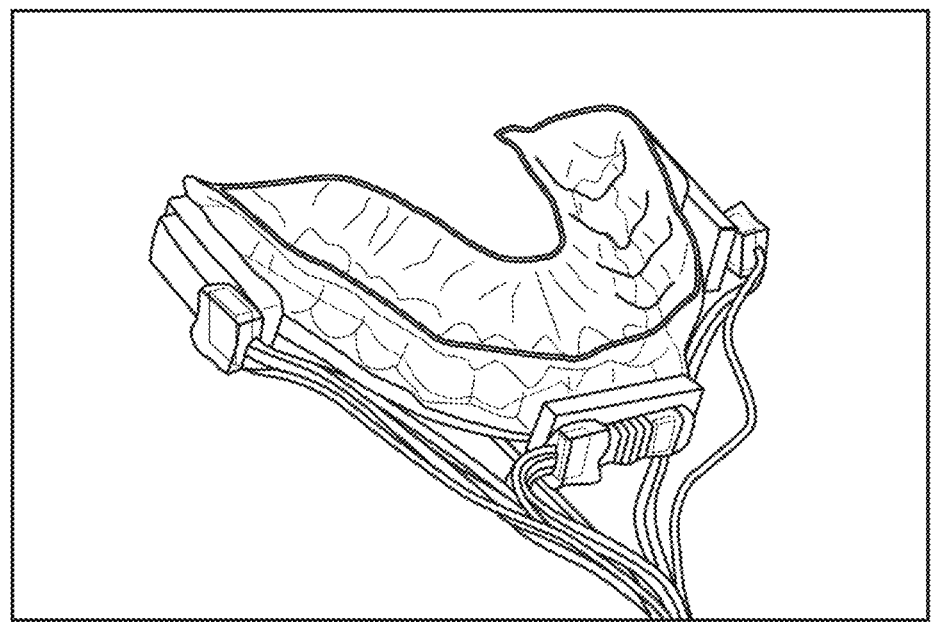
FIG. 23 displays an alternative configuration of the mouth guard of FIG. 22.

In another exemplary aspect, and as shown in FIG. 20, the bridge element 32 can be coupled to three receptacles 34 configured to receive a printed circuit board (PCB) assembly as described herein. In this aspect, the three receptacles 34 can be spaced about the mouth guard 10 and positioned at respective positions, such as, for example and without limitation, the three distinct locations disclosed herein. For example, a first receptacle can be positioned just outside the right molars of the subject, a second receptacle can be positioned just outside the left molars of the subject, and the third receptacle can be positioned just in front of the central incisors of the subject. In exemplary aspects, as shown in FIG. 22, each receptacle 34 can be configured to receive a respective PCB assembly. In these aspects, each PCB assembly can be affixed to the receptacles by medical-grade adhesive or another conventional adhesive, provided the adhesive is safe for usage within the mouth of a subject. It is further contemplated that the PCB assemblies, after being positioned within a respective receptacle, can be wired and sealed. An exemplary configuration of the PCB assemblies, the accelerometers, the bridge, and wiring of the mouth guard is depicted in FIG. 23. In exemplary aspects, it is contemplated that the bridge element 32 can define the three receptacles 34. In these aspects, it is contemplated that the three receptacles 34 can be integrally formed with the bridge element 32.

In operation, it is contemplated that the bridge element 32 can ensure that the accelerometers 30 are properly positioned. For example, it is contemplated that the bridge element 32 can be configured to ensure that the bottom edges of each receptacle 34 are positioned substantially within a common plane, such as, for example and without limitation, an xy plane. It is further contemplated that the receptacles 34 of the bridge element 32 can be spaced such that the left and right receptacles are substantially symmetrically positioned relative to the sagittal plane of the subject (containing the central axis 26 of the U-shaped element 12). It is still further contemplated that the center receptacle can be positioned such that it is substantially bisected by the sagittal plane of the subject (and the central axis 26 of the U-shaped element 12).

Optionally, in some exemplary aspects, it is contemplated that at least a portion of the mouth guard 10 can be printed with a 3-D printer. In these aspects, it is optionally contemplated that substantially the entire mouth guard can be printed with a 3-D printer. It is contemplated that the mouth guard can be printed as a single, integral piece or as multiple pieces to be assembled at a later time. It is further contemplated that the mouth guard can optionally comprise a single material. Alternatively, however, it is contemplated that the mouth guard can optionally comprise a plurality of materials. In exemplary aspects, it is contemplated that the receptacles for the PCB assemblies and other circuitry of the mouth guard can be printed with the 3-D printer. In some exemplary aspects, it is contemplated that at least a portion of the mouth guard can be printed with a 3-D printer and at least a portion of the mouth guard can be manufactured using a different manufacturing process, such as those further described herein. More generally, it is contemplated that at least a first portion of the mouth guard can be printed with a first manufacturing process as described herein and that at least a second portion of the mouth guard can be printed with a second manufacturing process as described herein.

Alternatively, it is contemplated that some combination of the manufacturing processes described above can be used to create the mouth guard.

Figure 24:
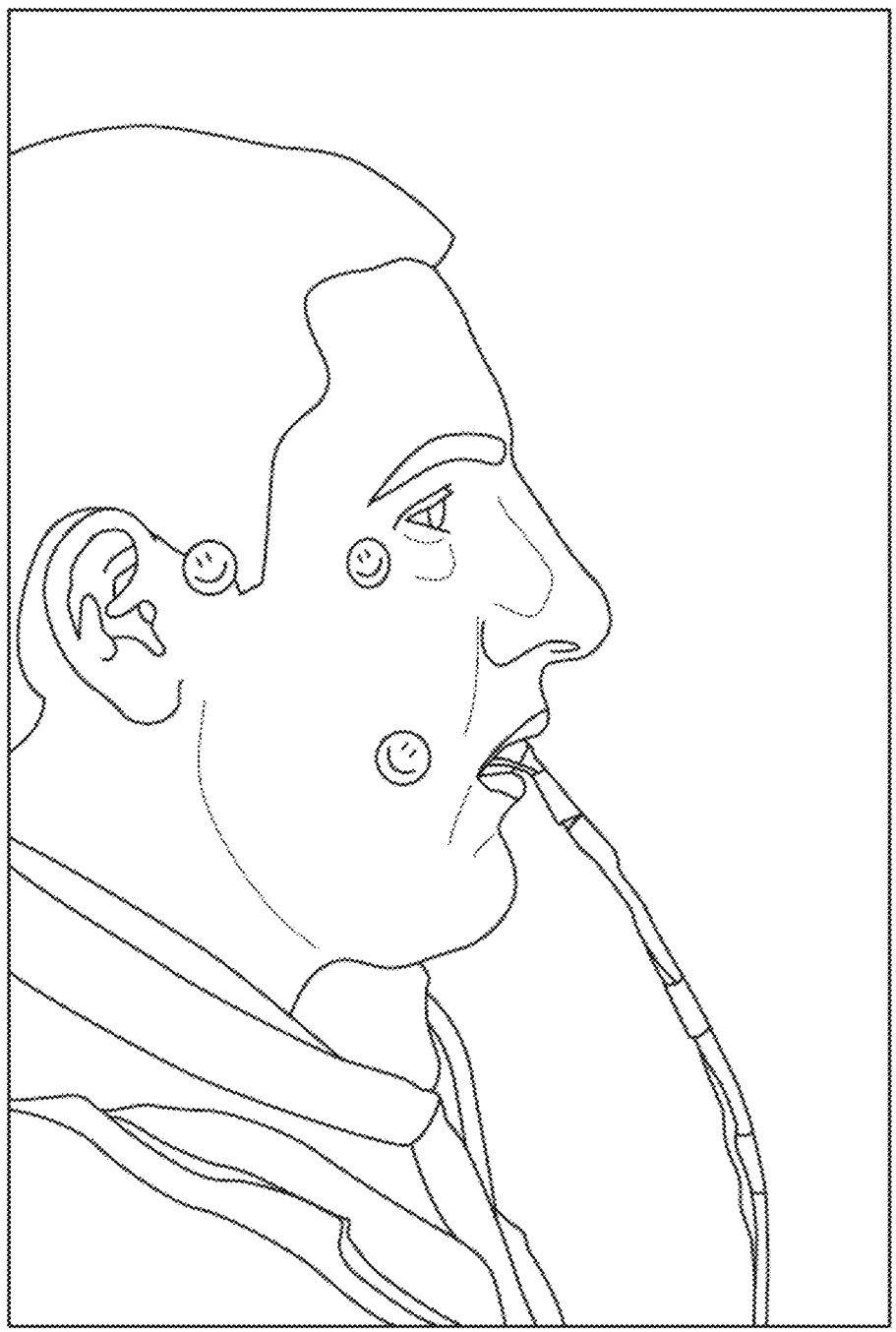
FIG. 24 depicts the use of biometric markers to determine the linear and angular positioning of a mouth guard relative to the head of a subject as disclosed herein.

As shown in FIG. 24, the linear and angular positions of the mouth guard 10 relative to the head of the subject can be identified using biometric markers. The center of mass of the head of the subject is positioned just beneath the zygomatic arch, just in front of the ear. The center of mass of the head of the subject can generally be found by running one's fingers along the crest of the cheekbone ridge that runs roughly from the eye socket (corresponding to the smiley face marker closest to the eye) back to the ear (corresponding to the smiley face marker closest to the ear). The left and right crest of the cheekbone ridge generally corresponds to the transverse plane of the head. The transverse plane intersects the sagittal plane, and a third plane, the coronal plane of the head, is orthogonal to those two planes. All three planes intersect at the center of mass of the head. The intersections of the planes form the fore-aft, left-right, and up-down directions of the head. The right PCB of the mouth guard can be positioned just inside the cheek and is found by palpating the cheek (corresponding to the lowest smiley face marker). It is contemplated that the front PCB can be visible if the subject's lips are parted. It is contemplated that other biometric markers may be identified as important for determining the severity of head impact.

Similar positional information for the head of the subject can be determined for the opposite (left) side of the head of the subject, and the positional values are then averaged to give the final positional information for the head of the subject. Using these average values, the linear and angular positions of the mouth guard relative to the head of the subject can be determined.

In use, and with reference to FIGS. 2 and 22-23, it is contemplated that the left PCB assembly (and associated accelerometers) can be configured to measure acceleration in the up-down and fore-aft directions, the right PCB assembly (and associated accelerometers) can be configured to measure acceleration in the up-down and fore-aft directions, and the central PCB assembly (and associated accelerometers) can be configured to measure acceleration in the left-right and up-down directions. The forward direction corresponds with the x direction, the leftward direction corresponds with the y-direction, and the upward direction corresponds with the z direction.

The Processing Circuitry

In a further aspect, and with reference to FIG. 1A, the plurality of accelerometers 30 of the mouth guard can be configured for operative communication with processing circuitry 50. In this aspect, the processing circuitry 50 can be configured to receive the outputs from the plurality of accelerometers 30 of the mouth guard 10. In exemplary aspects, the processing circuitry 50 can function as an integrated circuit. In other exemplary aspects, the plurality of accelerometers 30 and at least portions of the processing circuitry 50 can be embedded in or otherwise secured to the mouth guard.

In still a further aspect, the plurality of accelerometers 30 of the mouth guard 10 can be in operative communication with at least one power source 52. In this aspect, the at least one power source 52 can be in operative communication with the processing circuitry 50 such that the at least one power source is configured to power the accelerometers 30 of the mouth guard 10 and the processing circuitry. It is contemplated that the at least one power source 52 can be a conventional battery, capacitor, or electromagnetic power source. Optionally, it is further contemplated that the at least one power source 52 can be rechargeable through a first port defined in the mouth guard. It is still further contemplated that the at least one power source 52 can be removable and replaceable. In an exemplary aspect, it is contemplated that the at least one power source 52 can be an electric generator that is powered by mechanical energy received from the subject. In this aspect, it is contemplated that the electric generator can be configured to convert mechanical energy applied to the mouth guard by the subject (through, for example, biting down) into electrical energy. It is contemplated that the electric generator can optionally be a piezoelectric generator comprising one or more materials that exhibit the piezoelectric effect, such as, for example and without limitation, quartz. When coupled with appropriate circuitry, it is contemplated that such piezoelectric generators can be configured to generate electrical energy from cyclic mechanical strain.

In one aspect, the processing circuitry 50 can comprise at least one memory 64 in operative communication with the plurality of accelerometers 30 of the mouth guard 10. In this aspect, it is contemplated that the at least one memory 64 can be configured to receive and store the outputs of the plurality of accelerometers 30 of the mouth guard 10. In some aspects, the at least one memory 64 can be coupled to the mouth guard 10. However, in other alternative aspects, it is contemplated that the at least one memory 64 can be positioned at a remote location from the subject.

In another aspect, the processing circuitry 50 can comprise at least one transmitter 56 in operative communication with at least one of the at least one memory 64 and the plurality of accelerometers 30 of the mouth guard. In this aspect, it is contemplated that the at least one transmitter can be configured to transmit one or more outputs stored on the at least one memory. Optionally, it is contemplated that the at least one transmitter 56 can be a wireless transmitter configured to wirelessly transmit one or more outputs stored on the at least one memory. Alternatively, or additionally, it is contemplated that the at least one wireless transmitter can be configured to receive and then wirelessly transmit the outputs from the plurality of accelerometers of the mouth guard. Although a wireless transmitter is preferred, it is contemplated that the at least one memory and the plurality of accelerometers can be connected to one another by a conventional hard-wired connection.

In an additional aspect, it is contemplated that the processing circuitry 50 can comprise an analog-to-digital converter 54 as is conventionally known in the art. In this aspect, it is contemplated that the analog-to-digital converter 54 can be operatively coupled to and positioned between the plurality of accelerometers 30 and at least one of a memory 64 and a wireless transmitter 56. It is further contemplated that the analog-to-digital converter 54 can be configured to receive the outputs of the plurality of accelerometers 30 and convert the outputs into a digital signal configured for further processing by the processing circuitry.

In some optional aspects, the processing circuitry 50 can comprise a microcontroller/data logger 58 in operative communication with one or more components of the processing circuitry 50. In these aspects, it is contemplated that the microcontroller 58 can comprise hardware and software that are configured to control the operation of the components of the processing circuitry 50 in operative communication with the microcontroller. For example, it is contemplated that the microcontroller 58 can be configured to initiate transmission of outputs stored on the at least one memory 64.

In exemplary aspects, the processing circuitry 50 can optionally comprise a repeater 65 positioned on the person of the subject or in close proximity to the subject. In these aspects, the repeater 65 can be configured to receive the outputs of the plurality of accelerometers 30 of the mouth guard 10 from the at least one wireless transmitter 56 or through a hardwire connection. It is contemplated that the repeater 65 can be a relatively high-power repeater. In other exemplary aspects, the processing circuitry 50 can optionally comprise a receiver 66 configured to receive the outputs from the accelerometers 30 of the mouth guard 10 that are stored in the at least one memory 64 of the processing circuitry. In these aspects, it is contemplated that the receiver 66 can be configured to receive (i.e., download) the outputs that are stored in the memory 64 of the processing circuitry 50 in response to the occurrence of a threshold "trigger" event. It is further contemplated that the processing circuitry 50 and/or mouth guard 10 can define a second port configured to permit electrical coupling between the receiver 66 and the memory 64 of the processing circuitry such that the receiver can download the stored output values. It is still further contemplated that the processing circuitry 50 can operate in a relatively low-power state in which the outputs of the accelerometers 30 are not recorded until the occurrence of a threshold event, such as, for example and without limitation, acceleration at a rate higher than a predetermined threshold value. Upon occurrence of the threshold event, the processing circuitry 50 can shift to an active mode in which the outputs of the accelerometers 30 are recorded.

Optionally, in various aspects, it is contemplated that the processing circuitry 50 can comprise a base station that is positioned remotely from the subject. In these aspects, the wireless transmitter of the processing circuitry can optionally be configured to transmit the outputs (following analog-to-digital conversion, as appropriate) of the accelerometers to the base station. Alternatively, the base station can be operatively coupled to the repeater, and the outputs received by the repeater can be transmitted to the base station. In exemplary aspects, the base station can comprise a memory. Optionally, it is contemplated that the base station can be a computer 67 having a processor 68 and a memory 69 in communication with the processor. In exemplary aspects, the computer 67 can comprise a wireless receiver 66 configured to receive the outputs of the accelerometers.

The Helmet

In further aspects, and with reference to FIG. 1C, a helmet 40 can be provided for receiving at least a portion of the head of the subject. In these aspects, the helmet can have a wall 42 that defines an inner chamber 44. The inner chamber 44 of the helmet 40 can be configured to receive the head of the subject. In an additional aspect, the helmet 40 can comprise a plurality of accelerometers 46 operatively associated with the wall 42 of the helmet. In this aspect, the plurality of accelerometers 46 can be spaced from one another about the helmet 40. It is contemplated that each accelerometer 46 of the plurality of accelerometers can be configured to produce an output indicative of the linear and angular acceleration of the helmet.

In exemplary aspects, it is further contemplated that the helmet 40 can be operatively coupled to a plurality of accelerometers 46 and processing circuitry 50 in the manner described above with respect to the mouth guard 10. In these aspects, the processing circuitry 50 can be configured to convert the outputs from the plurality of accelerometers 46 into an output indicative of the linear and angular acceleration of the head of the subject.

In other exemplary aspects, the helmet 40 and the mouth guard 10 can be used simultaneously in a cooperative system 10 for determining the linear and angular accelerations of the head of the subject. In these aspects, it is contemplated that the helmet 40 and the mouth guard 10 can comprise the same number of accelerometers 30, 46. It is further contemplated that the accelerometers 46 of the helmet 40 can optionally be oriented and positioned in an orientation and position that generally corresponds to that of the accelerometers 30 of the mouth guard 10. Thus, in exemplary aspects, it is contemplated that the accelerometers 46 of the helmet can optionally be spaced about the helmet 40 within a common plane, which, optionally, can be parallel to the plane of the accelerometers 30 of the mouth guard 10. In these aspects, it is further contemplated that the accelerometers 46 can optionally be provided as clusters of at least one accelerometer, with each cluster of accelerometers positioned at a distinct location about the helmet. It is further contemplated that the accelerometers 46 can optionally be provided in three clusters of at least one accelerometer, with each cluster being positioned at a distinct location. Optionally, the distinct locations can comprise a first location proximate the right side of the head of the subject, a second location proximate the left side of the head of the subject, and a third location proximate a center portion of the head of the subject, such as, for example and without limitation, a location proximate the forehead of the subject or a location proximate the back or rear portion of the head of the subject. In further exemplary aspects, it is contemplated that at least portions of the processing circuitry 50 can be in operative communication with the accelerometers 30, 46 of both the mouth guard 10 and the helmet 40. Alternatively, the mouth guard 10 and the helmet 40 can be in operative communication with distinct sets of processing circuitry as described herein.

Exemplary Methods

In use, the helmet and/or mouth guard, in conjunction with the processing circuitry, can be used in a method for determining the linear and angular acceleration of the head of the subject. In one aspect, the head of the subject can be positioned within the inner chamber of the helmet. In another aspect, the mouth guard can be positioned in engagement with at least one of the upper teeth and the lower teeth of the subject. In an additional aspect, the method can comprise delivering a first impact force to the helmet. In response to delivery of the first impact force, each accelerometer of the plurality of accelerometers of the helmet can be configured to produce an output indicative of the linear and angular acceleration of the helmet. Similarly, each accelerometer of the plurality of accelerometers of the mouth guard can be configured to produce an output indicative of the linear and angular acceleration of the mouth guard. Thus, the accelerometers of the helmet and the mouth guard can simultaneously record impact and acceleration data. It is contemplated that the accelerations measured by the accelerometers 30 of the mouth guard 10 substantially correspond to the accelerations actually experienced by the head of the subject.

In a further aspect, the method can comprise transmitting the outputs of the accelerometers of the helmet and the mouth guard to the processing circuitry. In another aspect, the method can comprise determining, through the processing circuitry, a transfer function configured to convert the outputs of the accelerometers of the helmet to the outputs of the accelerometers of the mouth guard. In this aspect, it is contemplated that this step can be repeated for a series of impact forces that are applied to the helmet in order to improve the accuracy of the transfer function.

In an additional aspect, the method can comprise disengaging the mouth guard from the teeth of the subject and, subsequently, removing the mouth guard from the mouth of the subject. In this aspect, it is contemplated that, after the transfer function is known, the acceleration and impact experienced by the head of the subject can be determined based solely on the acceleration and impact data recorded by the accelerometers of the helmet; thus, the subject does not have to continue wearing the mouth guard. In still another aspect, the method can comprise delivering a second impact force to the helmet. In response to delivery of the second impact force, each accelerometer of the plurality of accelerometers of the helmet can be configured to produce an output indicative of the linear and angular acceleration of the helmet.

In still another aspect, the method can comprise transmitting the outputs of the accelerometers of the helmet to the processing circuitry. In a further aspect, the method can comprise applying, through the processing circuitry, the transfer function to the outputs of the accelerometers of the helmet to determine the acceleration of the head of the subject.

In another exemplary method, it is contemplated that a database of head acceleration event characteristics, head injuries, treatments, and results can be developed into a tool for providing information to a subject regarding diagnosis, suggested treatment, and prognosis. The acceleration event characteristics within the database can include peak linear and angular accelerations recorded for the subject, the duration of an acceleration above a predetermined threshold, and other characteristics that provide information regarding the amount and types of accelerations experienced by the head of the subject. In one aspect, in operation, the method can comprise downloading head acceleration outputs from the plurality of accelerometers of a mouth guard and/or a helmet as described herein. In this aspect, the method can further comprise, through a processor in communication with the database, determining possible head injuries and/or symptoms associated with the acceleration outputs. In another aspect, the method can comprise providing an input to the database indicative of symptoms exhibited by a subject. In this aspect, the method can further comprise, through a processor in communication with the database, determining possible treatments and associated prognoses for the symptoms exhibited by the subject. Typically, in operation, it is contemplated that a medical technician can download the acceleration outputs from the mouth guard and/or the helmet, the acceleration data can be evaluated using the database, and treatment of the subject can be initiated in the trauma center or even during transport of the subject to the trauma center. In exemplary sports applications, it is contemplated that, after an impact during a game, the acceleration data from the mouth guard and/or helmet can be downloaded and evaluated to determine if an athlete should be allowed to return to play. It is contemplated that the downloaded acceleration information can be particularly useful when the subject is unconscious or otherwise unable to report symptoms or aid in diagnosis. It is still further contemplated that conscious athletes or soldiers are often eager to return to play or duty and are uncooperative or dismissive of suggestions of the severity of the traumatic injury they have experienced. Thus, it is contemplated that the use of the downloaded acceleration data can help inform physicians, coaches, and officials of the severity of the head injury experienced by the subject.

In further exemplary aspects, it is contemplated that the disclosed mouth guard and/or helmet can be worn by all athletes participating in regulated play and all soldiers participating in training or combat. For example, in boxing, where a knockout determines the outcome of a fight, it is contemplated that the disclosed devices, systems, and methods can be used to verify the legitimacy of a knockout based upon the recorded acceleration data. In another exemplary application, the disclosed devices, systems, and methods can be used during rehabilitation of soldiers, stroke victims, and other patients with compromised balance to ensure that any head traumas of the patient are recorded. It is further contemplated that, because specific motions of the head can be related to compromised balance, head injury, and falls, the disclosed devices, systems, and methods can be used in diagnostics, therapy, and monitoring of individuals with verified or suspected compromised balance or head injury. In still further exemplary applications, it is contemplated that parents can require their children to wear the disclosed devices during activities associated with a significant risk of head impact, such as, for example, skateboarding and bicycle riding.

The Algorithm for Analyzing Acceleration Data from the Mouth Guard and/or Helmet An exemplary algorithm for analyzing acceleration data from the mouth guard is described below. Although the algorithm is described with respect to a mouth guard configuration in which three three-axis accelerometers were used, it is contemplated that a similar overall method can be adapted to any accelerometer configuration described herein.

Each 3-axis accelerometer of the mouth guard can have a local orthogonal 3-axis accelerometer coordinate system that is configured to measure the linear accelerations in the directions of those coordinate axes. The algorithm for analyzing the acceleration data is determined by the following procedure: 1) Establishing an orthogonal local mouth guard coordinate system (for example, oriented in the forward, left side, and upward directions with the forward and left side directions in the plane of the bite of the molars and the upward direction perpendicular to that plane); 2) Determining the position and orientation of each local 3-axis accelerometer coordinate system in the local mouth guard coordinate system; 3) Transforming the 3-axis accelerometer measured linear accelerations to the local mouth guard coordinate system; 4) Determining the angular accelerations of the mouth guard in the local mouth guard coordinate system from the linear accelerations in the local mouth guard coordinate system; 5) Determining the linear accelerations of the origin of the local mouth guard coordinate system in the local mouth guard coordinate system; 6) Determining the position of the head center of mass and establishing an orthogonal local head coordinate system with its origin at the head center of mass (for example, oriented in the forward, left side, and upward directions); 7) Determining the position and orientation of the local mouth guard coordinate system in the local head center of mass coordinate systems; 8) Transforming the angular accelerations in the local mouth guard coordinate system to the angular accelerations in the local head center of mass coordinate system; and 9) Determining the linear accelerations of the head center of mass in the local head center of mass coordinate system from the mouth guard linear and angular accelerations in the local mouth guard coordinate system. In exemplary aspects, it is contemplated that steps 3) through 9) can be mathematically combined into a single step. It is contemplated that the acceleration of points other than the center of mass may be identified as important for determining the severity of head impact and can be determined using similar methods.

As shown in FIG. 1A, the mouth guard can optionally comprise power supplies, accelerometers, analog-to-digital converters, transmitters, data loggers, amplifiers, and/or antennas as are known in the art. However, it is contemplated that the way in which the acceleration data is stored and recovered can significantly impact the complexity, size and power requirements of the device. For example, it is contemplated that storing the data for downloading using a hardwire connection at a later time can significantly reduce the complexity, size and power requirements of the mouth guard electronics.

It is contemplated that the minimum number of accelerometers required to determine the angular and linear accelerations of the head center of mass (or other point) is six. It is further contemplated that if only linear accelerometers are used, those six linear accelerometers are most conveniently configured as three 2-axis accelerometer packages that are substantially aligned with the local orthogonal mouth guard coordinate system axes as shown in FIG. 2. It is still further contemplated that this configuration can significantly decrease the complexity of the device by reducing the number of accelerometers from nine to six, significantly decrease the amount of data collected from the accelerometers by reducing the number of channels from nine to six, significantly decrease the complexity and amount of the data analysis, and significantly increase the accuracy of the linear and angular accelerations of the head center of mass (or other point) results. It is contemplated that the data analysis algorithm for the three 2-axis accelerometer configuration can be substantially the same as the three 3-axis accelerometer configuration except that steps 1-3 can be simplified.

As shown in FIG. 2, six linear accelerometers, two on the right side of the mouth guard, two center accelerometers, and two left accelerometers, can be used to measure the linear accelerations $a_{Rx}, a_{Rz}, a_{Cy}, a_{Cz}, a_{Lx}$, and $a_{Lz}$. The xyz axes are orthogonal. The accelerometers lie on the xy plane and are positioned symmetrically relative to the xz plane. The accelerometer measurement axes are parallel to the xyz axes. The length of the mouth guard measured from the midpoint between the two left accelerometers and two right accelerometers to the two center accelerometers is $d_x$, and the width of the mouth guard measured from the two left accelerometers to the two right accelerometers is $d_y$. Rigid body kinematic analysis can be used to determine the angular and linear accelerations of the mouth guard at the origin O from the measured linear accelerations. In the mouth guard coordinate system xyz, if the linear acceleration terms due to the angular velocities are ignored, the angular accelerations $\alpha_x, \alpha_y$, and $\alpha_z$ can be determined from the linear accelerations $a_{Rx}, a_{Rz}, a_{Cy}, a_{Cz}, a_{Lx}$, and $a_{Lz}$ using the following equations:

$$\alpha_x = (a_{Lz} - a_{Rz})/d_y, \; \alpha_y = \left(\frac{a_{Rz} + a_{Lz}}{2} - a_{Cz}\right)/d_x, \text{ and } \alpha_z = (a_{Rx} - a_{Lx})/d_y.$$

In the mouth guard coordinate system xyz, if the linear acceleration terms due to the angular velocities are ignored, the linear accelerations of point O, $a_{Ox}, a_{Oy}$, and $a_{Oz}$, can be determined using the following equations: $a_{Ox}=(a_{Lx}+a_{Rx})/2$, $a_{Oy}=a_{Cy}-\alpha_z d_x=a_{Cy}-(a_{Rx}-a_{Lx})d_x/d_y$, and $a_{Oz}=(a_{Lz}+a_{Rz})/2$. It is contemplated that these accelerations of the mouth guard can be used to determine the acceleration of any point on the skull, including the head center of mass.

Figure 3:
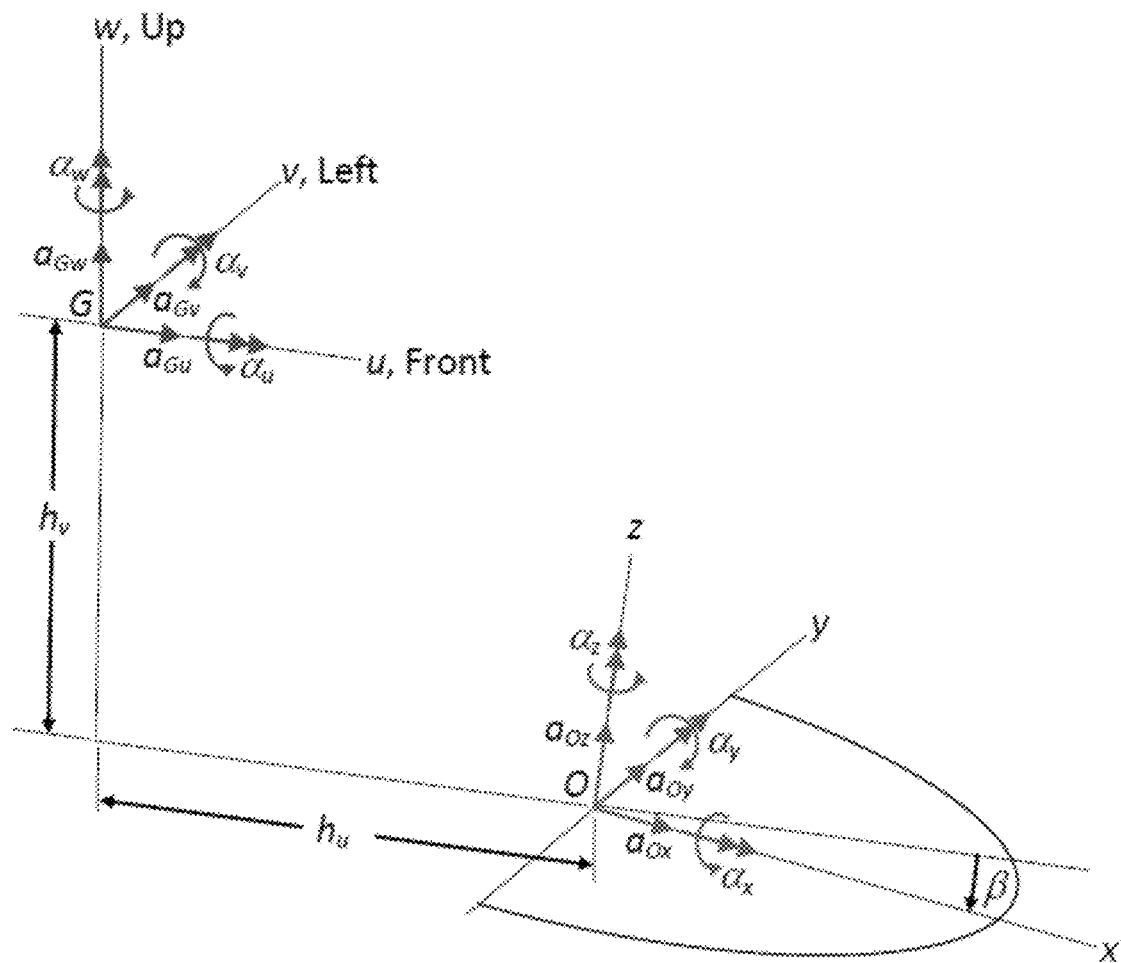
FIG. 3 depicts an exemplary local mouth guard coordinate system having axes x, y, and z and origin O relative to the head coordinate system axes u, v, and w and origin and center of mass G. The accelerations of the head center of mass are indicated by the arrows originating from point G.

FIG. 3 shows the head coordinate system axes u, v, and w and origin and center of mass G relative to the local mouth guard coordinate system axes x, y, and z and origin O. The uvw axes are orthogonal. They and v axes are parallel, and the xz and uw planes and origins O and G are on the sagittal plane. The u axis points forward, the v axis points leftward, and the w axis points upward. The approximate location of the head center of mass is found by following the left and right zygomatic ridge back to just in front of the ear—the head center of mass is located between those two points on the sagittal plane, and those two points lie on the v axis. The plane formed by the left and right zygomatic arches and the sagital plane intersect along the u axis. The xyz coordinate system is rotated an angle β relative to the uvw coordinate system. The xyz origin O is a distance $h_u$ in the forward or u direction and a distance $h_w$ in the downward or negative w direction from the uvw origin G. The head center of mass coordinate system origin G and axes uvw are used as the reference coordinate system origin and axes to compare head accelerations from one individual to the next. If the head and mouth guard system is treated as a rigid body, then the angular accelerations of the head center of mass, $\alpha_u, \alpha_v$, and $\alpha_w$, are as follows: $\alpha_u=\alpha_x \cos(\beta)+\alpha_z \sin(\beta)$, $\alpha_v=\alpha_y$, and $\alpha_w=-\alpha_x \sin(\beta)+\alpha_z \cos(\beta)$. If the linear acceleration terms due to the angular velocities are ignored, the linear accelerations of the head center of mass, $a_{Gu}, a_{Gv}, a_{Gw}$, are as follows: $a_{Gu}=a_{Ox} \cos(\beta)+a_{Oz} \sin(\beta)+h_v \alpha_v$, $a_{Gv}=a_{Oy}-h_u \alpha_u-h_u \alpha_w$, and $a_{Gw}=-a_{Ox} \sin(\beta)+a_{Oz} \cos(\beta)+h_u \alpha_v$. The accelerations of the head center of mass, $\alpha_u, \alpha_v, \alpha_w, a_{Gu}, a_{Gv}$, and $a_{Gw}$ can be used to determine the severity of a head impact.

The following examples are offered by way of illustration and not by way of limitation.

Experimental Example One

The accelerations of the head during soccer ball heading were recorded by introducing a mouth guard instrumented with a dual-axis linear accelerometer chip. The accelerometer chip was hardwired to a data acquisition unit and powered by a chemical battery.

Increasing concern about health and safety in youth sports has brought attention to the possible cumulative head trauma of soccer ball heading. Studies into a possible correlation between soccer heading and cognitive dysfunction, the effectiveness of soccer headgear, and the acceleration of the head during the heading maneuver are well-documented. Paris et al., "Soccer Ball Heading Model," Proceedings of the ASME 2008 Summer Bioengineering Conference (SBC2008) June 25-29, Marriott Resort, Marco Island, Fla., USA (2008), which is incorporated by reference herein in its entirety, proposed an impulse momentum formulation to model the impact between the soccer ball and the head. To verify the theory, a soccer ball was dropped on a solid resin sphere of equal radius and fixture on a force plate. The numerical results of the model agreed well with the experimental results for impact force, impact duration, and impulse vs. impact velocity. The analytical model effectively represented the impact of a soccer ball on a rigid spherical surface of equal diameter.

Figure 4:
FIGS. 4-5B display an experimental setup that was used to investigate the accelerations of the head during soccer ball heading. The accelerations were measured using an exemplary accelerometer chip operatively associated with a mouth guard as disclosed herein.

The test subject was an 18-year-old male in good physical condition, 168 cm tall and with a mass of 70 kg. The subject was asked perform a proper heading maneuver on a ball that would be launched toward his head. A soccer player performing a heading motion usually jumps and moves the head anteriorly in an offensive movement, causing a much greater impulse on the head than if he or she stood still. Such a motion includes adducting the neck in the sagittal plane simultaneously with the impact of the ball (FIG. 4).

Figure 5A:
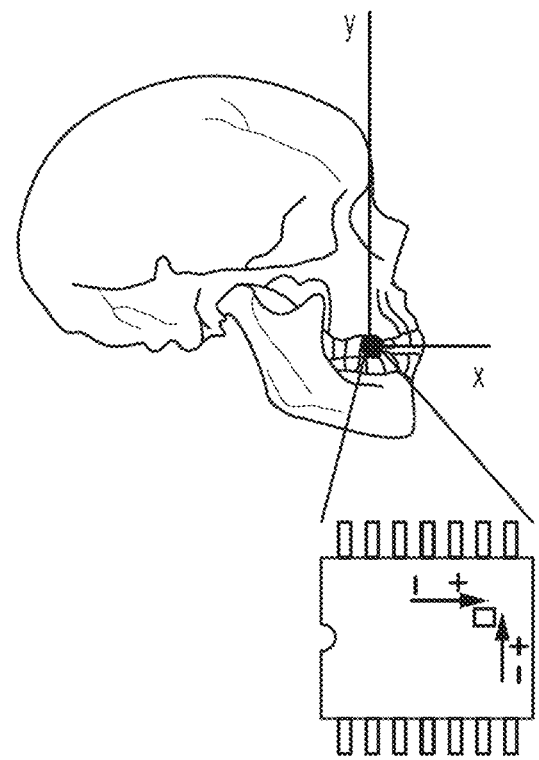
Figure 5B:
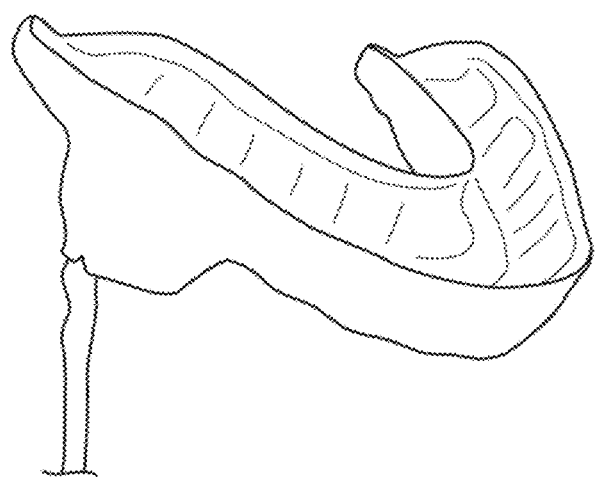

A Baden 150 soccer ball, inflated to 55 kPa, was used. A JUGS® Soccer Machine was used to deliver the ball at four different launch speeds. The subject was fitted with a custom acrylic mouth guard that encased an AD ADXL250 Dual Axis Accelerometer Chip with the X-axis oriented anteriorly and the Y-axis superiorly (FIGS. 5A and 5B). The accelerometer was wired to a DATAQ data acquisition unit and an HP laptop with DATAQ data acquisition software. All experimental trials were performed indoors to eliminate the effects of wind.

The subject stood at four different distances from the launcher to carry out the heading maneuver at four different launch speeds. Approximate impact velocities were calculated based on the initial velocity and projectile kinematics. The DATAQ software sampled at 10 kHz. The output voltage amplitude was directly proportional to the magnitude of the acceleration of the chip. One g (9.81 m/s/s) corresponded to 0.38 mV output.

Each set of impact data was isolated and smoothed using a five-point moving average since the period of the noise was usually three to four samples long. From this smoothed data, the peak positive and negative accelerations were averaged and plotted against velocity.

Figure 6:
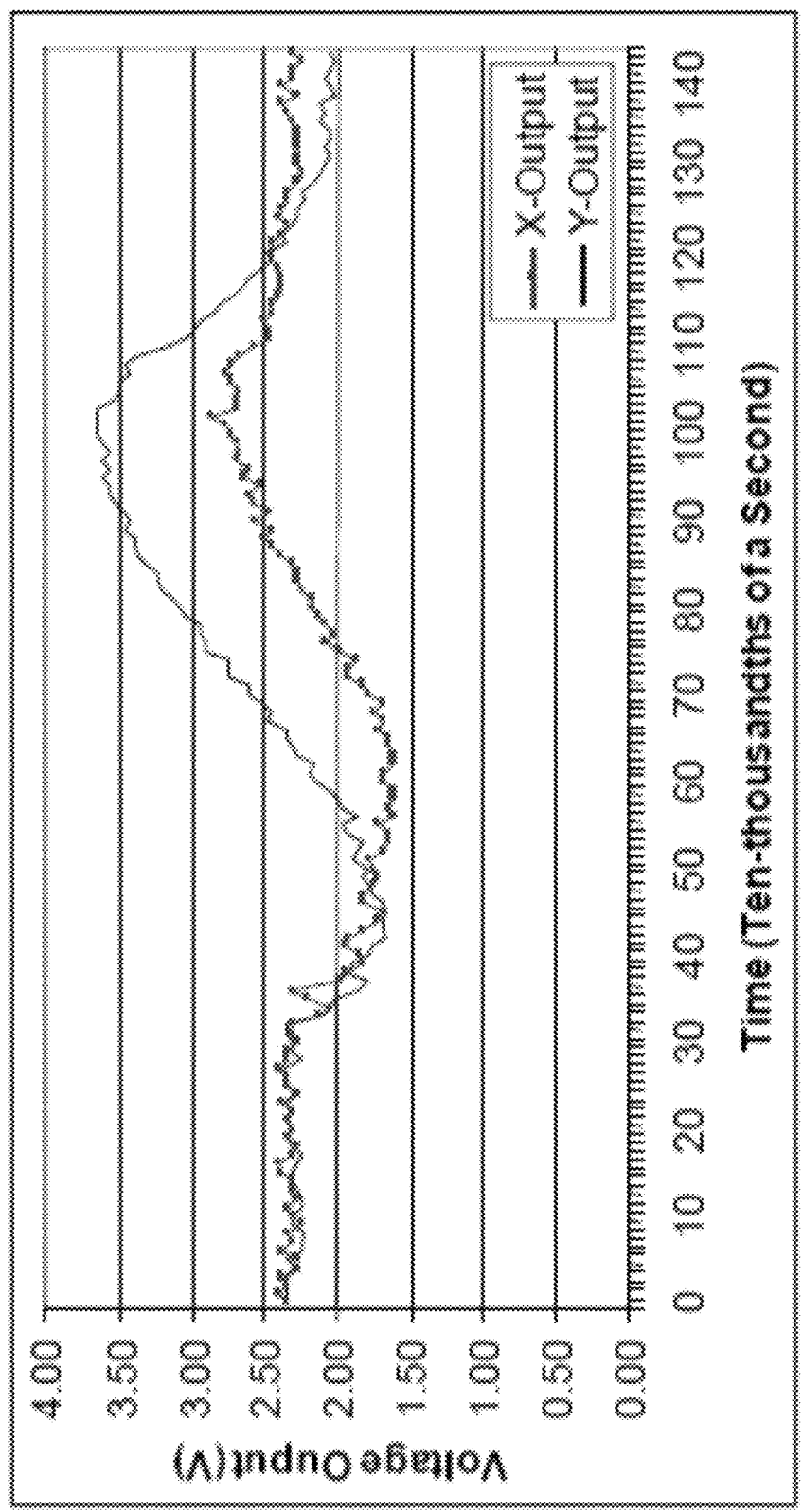
FIGS. 6-8 display the experimental acceleration data that were measured using the experimental setup of FIGS. 4-5B.
Figure 7:
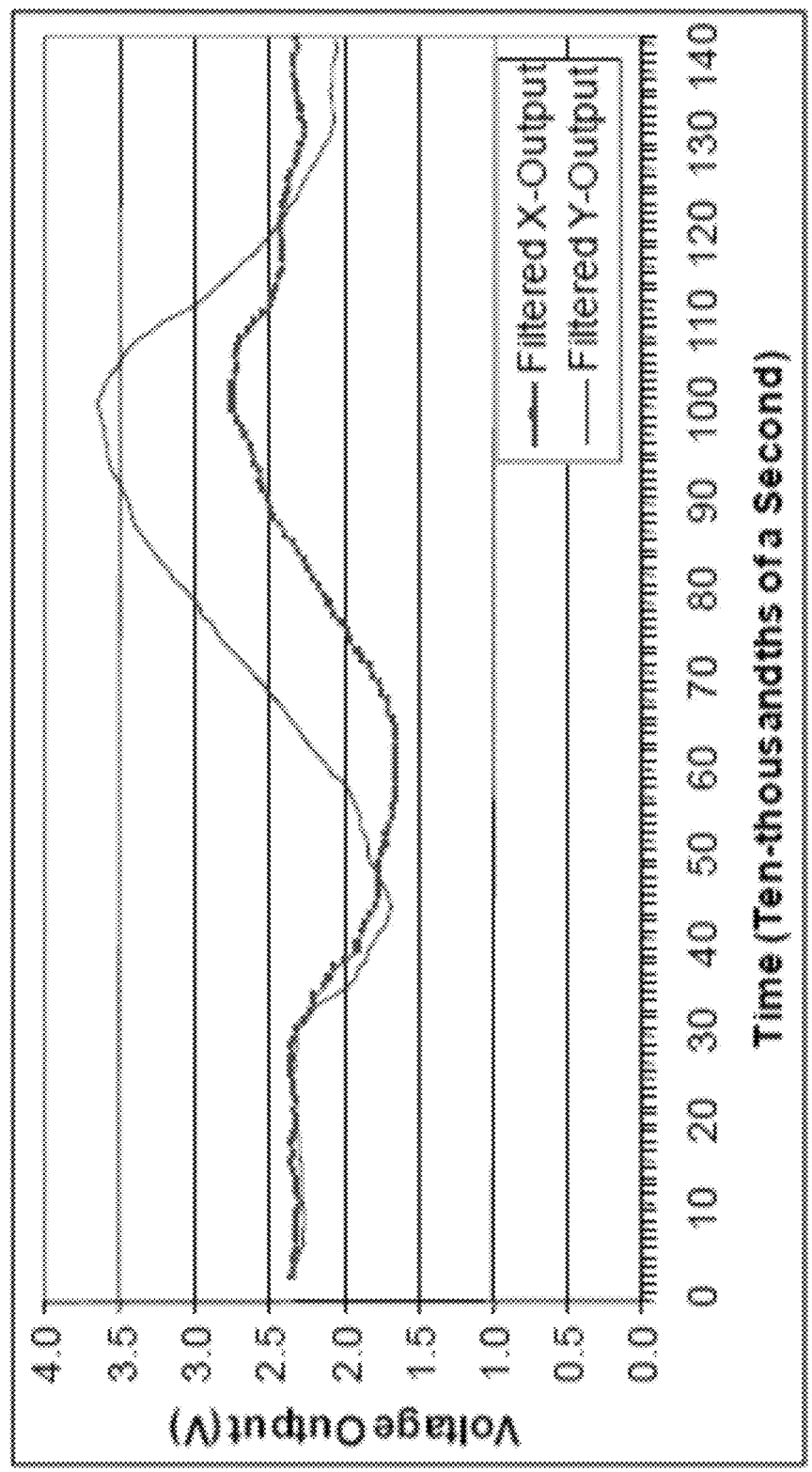
Figure 8:
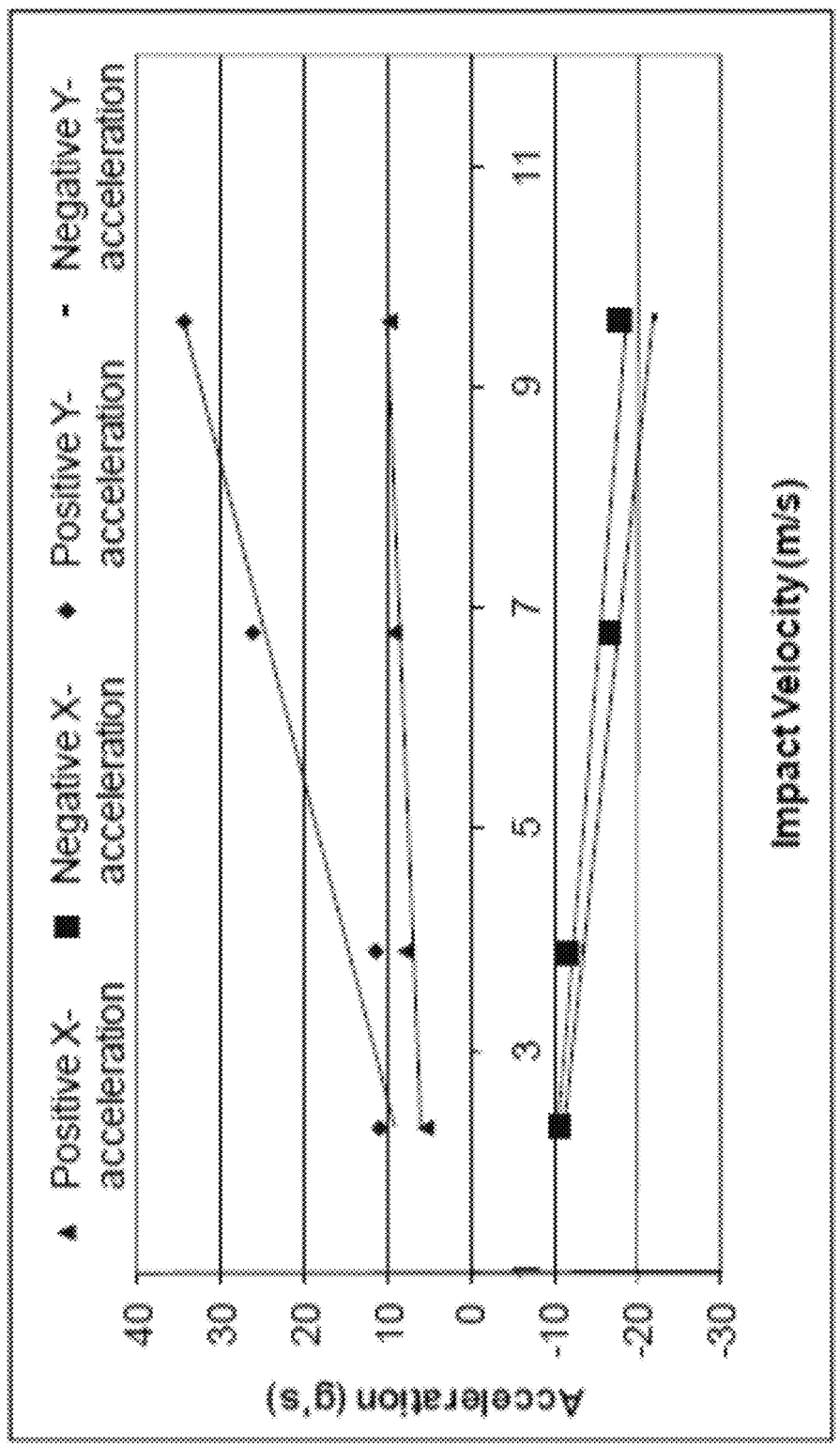
Figure 9:
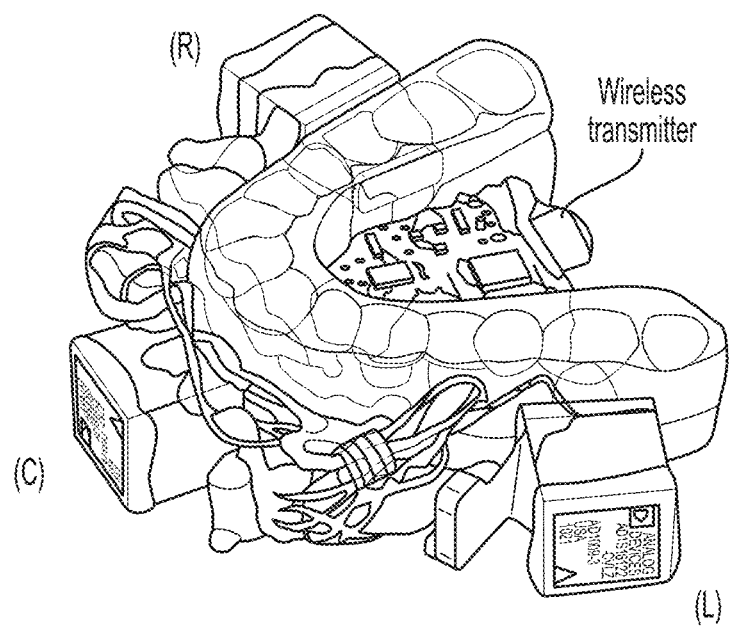
FIGS. 9-10 and 12 display an experimental setup that was used to measure accelerations of the head resulting from impact forces that occur during soccer ball heading.

FIG. 6 shows unfiltered data from a 9.6 m/s impact. FIG. 7 shows the same data filtered by a five-point moving average. Here, the peaks are more defined and are not just spikes from noise. All the peak accelerations for each velocity were averaged and graphed against velocity with best fit linear trend lines in FIG. 8.

The results demonstrated the use of an accelerometer-chip instrumented mouth guard. A maximum 34 g's of head acceleration was observed from a mere 11.2 m/s ball launch. It has been suggested that most heading maneuvers are performed on balls traveling at up to 18.1 m/s, which would cause even greater head accelerations. Even though the duration of such accelerations is on the order of only a few milliseconds, there is concern that the repetitive nature of heading may cause neuro-cognitive damage.

The data demonstrated a high correlation between maximum head acceleration and impact velocity. The data also showed a relationship consistent with that presented in the numerical impulse-momentum model and experimental results discussed by Paris et al. (2008).

Experimental Example Two

The following experimental example is further described in Kara et al., "Evaluation of an Instrumented Mouthguard to Measure the Accelerations of the Head due to Soccer Ball Heading," Proceedings of PACAM XII, 12th Pan-American Congress of Applied Mechanics (Jan. 2-6, 2012, Port of Spain, Trinidad), which is incorporated by reference herein in its entirety.

An exemplary mouth guard with nine spatially separated accelerometers configured as three spatially-separated three-axis accelerometers and a microcontroller with a data logger and a wireless transmitter was built and tested.

Recent concern about the potential cumulative effects of head impacts, even those not severe enough to cause loss of consciousness, in youth, college, amateur and professional athletes has led to increased research in this area. Soccer is a unique sport in that the unprotected head is deliberately used to direct the motion of the ball during play. Head injuries account for approximately 4-15% of all injuries experienced by soccer players, depending on the population surveyed. While the possible long-term effects of heading are still subject to debate, there is evidence which suggests that it is responsible for transient neurocognitive deficits and transient concussion symptoms. In order for the highest-risk sports and individuals to be identified, tools are needed that can quantitatively measure the levels of head acceleration experienced by athletes in a variety of situations.

This experimental example tested a wireless, instrumented mouth guard that was capable of measuring accelerations of the head resulting from impact forces, specifically resulting from soccer ball heading. In the work presented here, three 3-axis accelerometers were used, allowing both linear and angular accelerations of the head to be determined. It is contemplated that such instrumentation can (1) provide insight into the still-debated issue of whether heading is potentially dangerous by directly examining the biomechanics of heading, and (2) lead to the development of instrumentation that could potentially provide the means for quantitative assessment of any type of head impact injury.

Figure 10:
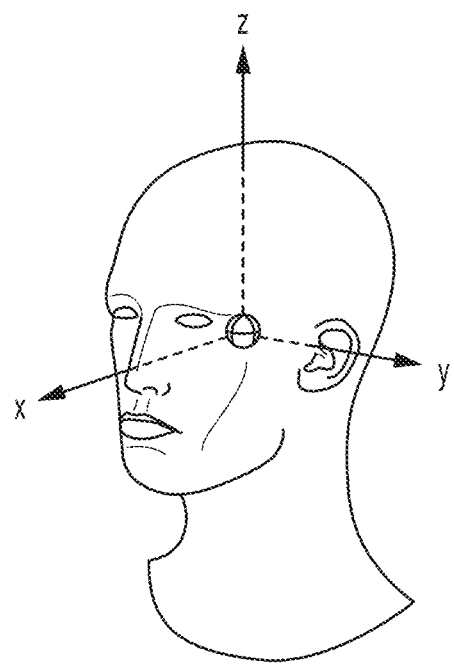

The subject of this research was an 18-year-old female soccer player in good physical condition, with a height of 175 cm and a mass of 69 kg. A custom acrylic mouth guard, pictured in FIG. 9, was created from a mold of the subject's teeth and instrumented with three 3-axis microelectromechanical system (MEMS) accelerometers (Analog Devices, ADIS16223). These accelerometers, labeled (R), (C) and (L) in FIG. 9, were capable of measuring large accelerations with high acquisition rates (±70 g, 14 kHz), and were small enough in mass to avoid significant inertial effects on the player's head. Referring to FIG. 10, the accelerometers were used to determine the linear accelerations of the subject's head in the x-, y- and z-directions, and the spatial separation of the accelerometers allowed the angular accelerations about the x-, y- and z-axes, as well as the linear accelerations of the subject's head center of mass, to be determined. The mouth guard contained a wireless transmitter, labeled in FIG. 9, which sent data to a wireless data logger connected to a laptop computer. The wireless aspect of this device allowed the subject to move normally without being tethered to a data acquisition system.

During experimentation, a soccer ball launching machine (Sports Soccer Machine M1800, Jugs Sports Equipment) was used to launch balls at the test subject, who was asked to perform heading maneuvers consistent with those ordinarily performed during practice and game play. The balls were launched at speeds up to approximately 12 m/s. A standard size 5 soccer ball, inflated to 62 kPa, was used. Experiments were performed indoors to eliminate the effects of wind. Each heading event was recorded using a high speed (HS) camera (HotShot 512 INT, NAC Image Technology) capable of recording up to 2,000 fps at its full resolution of 512×512 pixels. Contact between the ball and head typically lasted tens of milliseconds, allowing between 20 and 30 frames to be captured over the course of the impact. This allowed the time evolution of the ball geometry, as well as the ball and head positions and the impact force between the two, to be studied in much greater detail. Frame-by-frame analysis of each video was performed using the Image Processing Toolbox available with MATLAB. The position of the ball was determined in each frame, as well as its geometric deflection during contact with the head. The pre- and post-impact velocities, and the impulse delivered by the ball to the head, were calculated from this information.

Figure 11:
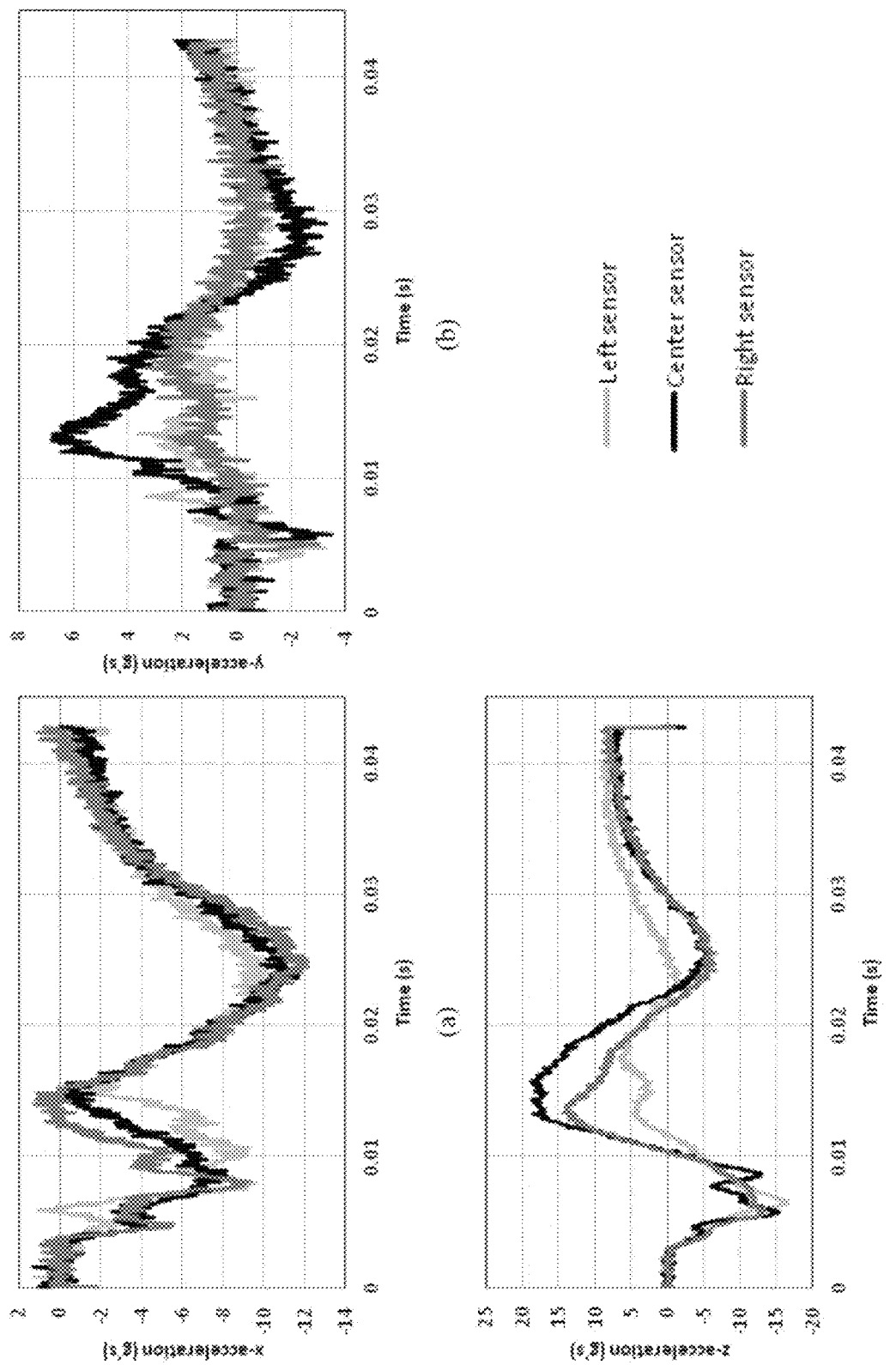
FIGS. 11 and 13-18 display the experimental force and acceleration data that were measured using the experimental setup of FIGS. 9-10. The force and impulse data shown in FIGS. 13 and 14 were derived from frame-by-frame analysis of high-speed video. A representative frame of the high-speed video is depicted in FIG. 12. The acceleration data shown in FIGS. 11 and 15-18 were derived from the output of the mouth guard shown in FIG. 9.
Figure 12:
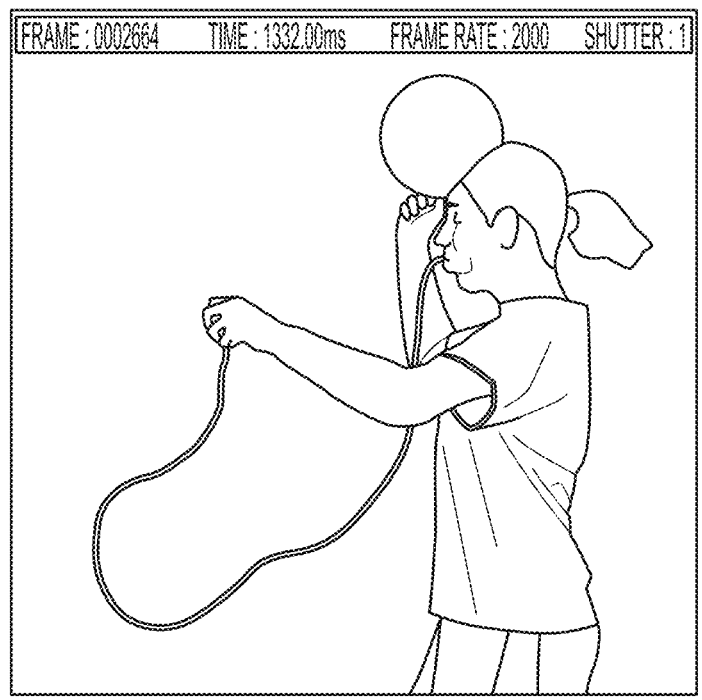
Figure 13:
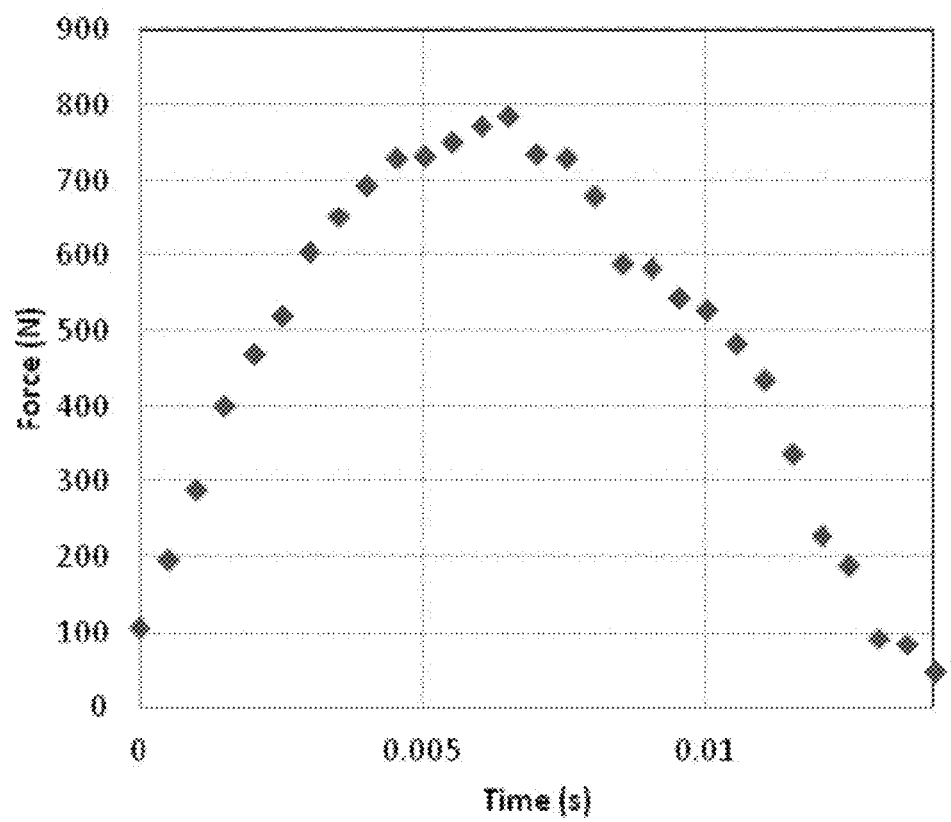
Figure 14:
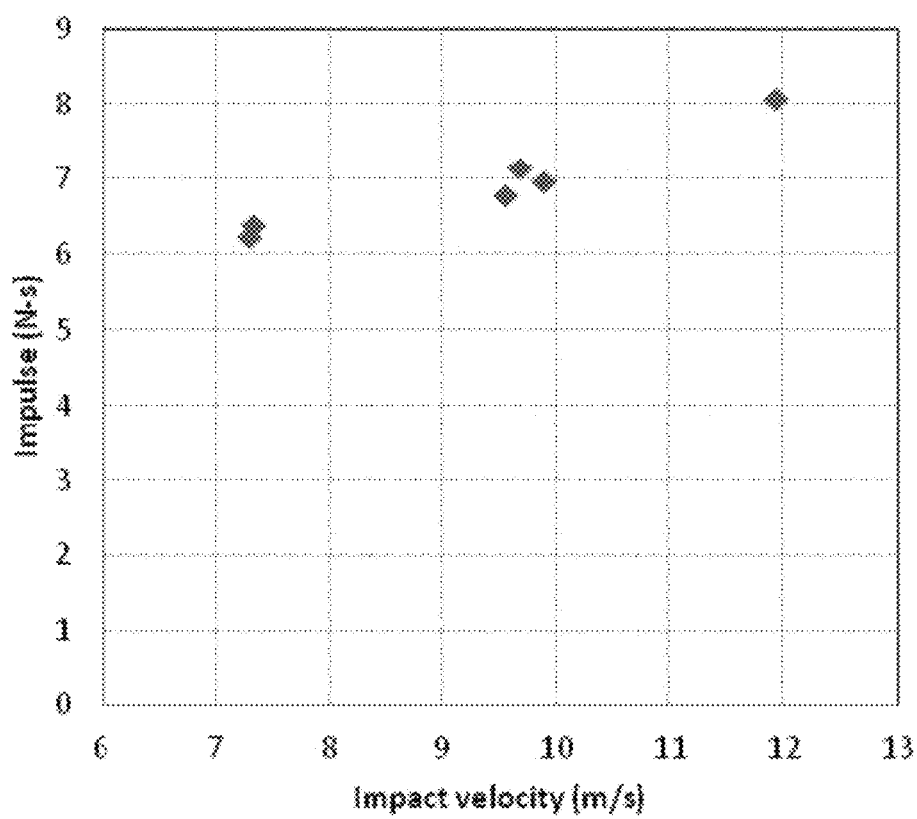

An example of the type of data collected for a typical heading event is presented here. The coordinate system used to describe the acceleration results is shown in FIG. 10. The center of mass (CG) of the head was assumed to lie at the sagittal plane, approximately beneath the zygomatic arch. The raw data collected by the mouth guard for each heading event included linear accelerations in the x-, y- and z-directions for each of the three attached accelerometer sensors in the local coordinate system for that sensor. FIG. 11 shows transformed accelerometer traces for the global x-, y- and z-directions (FIG. 10) from each sensor for one particular heading event. Frame-by-frame analysis of the HS video captured during this heading event reveals that the absolute value of ball velocity was approximately 9.9 m/s pre-impact, and approximately 7.4 m/s post-impact. A single frame from the HS video captured for this event, showing the maximum geometric deformation of the ball, is shown in FIG. 12. For the heading event pictured in FIG. 12, the HS camera captured 26 frames where the ball and head were in contact, making the duration of the impact equal to approximately 13 ms. The force F delivered to the head from the ball was determined as a function of time throughout the heading event using $F=p\pi d^2/4$, where p is the pressure in the ball and d is the diameter of the contact patch between the ball and the player's head measured from the HS video. In this case, the ball pressure was 62 kPa. Change in pressure was neglected. The force imparted to the head by the ball is shown in FIG. 13 as a function of time. The total impulse delivered by the ball was calculated by integrating the force shown in FIG. 12 as a function of time over the course of the entire impact. This integration yielded a total impulse of 7.01 N-s for the profile shown in FIG. 12. As a validation of the impulse, the impulse was compared with the change in momentum of the ball, and very good agreement was found.

Figure 15:
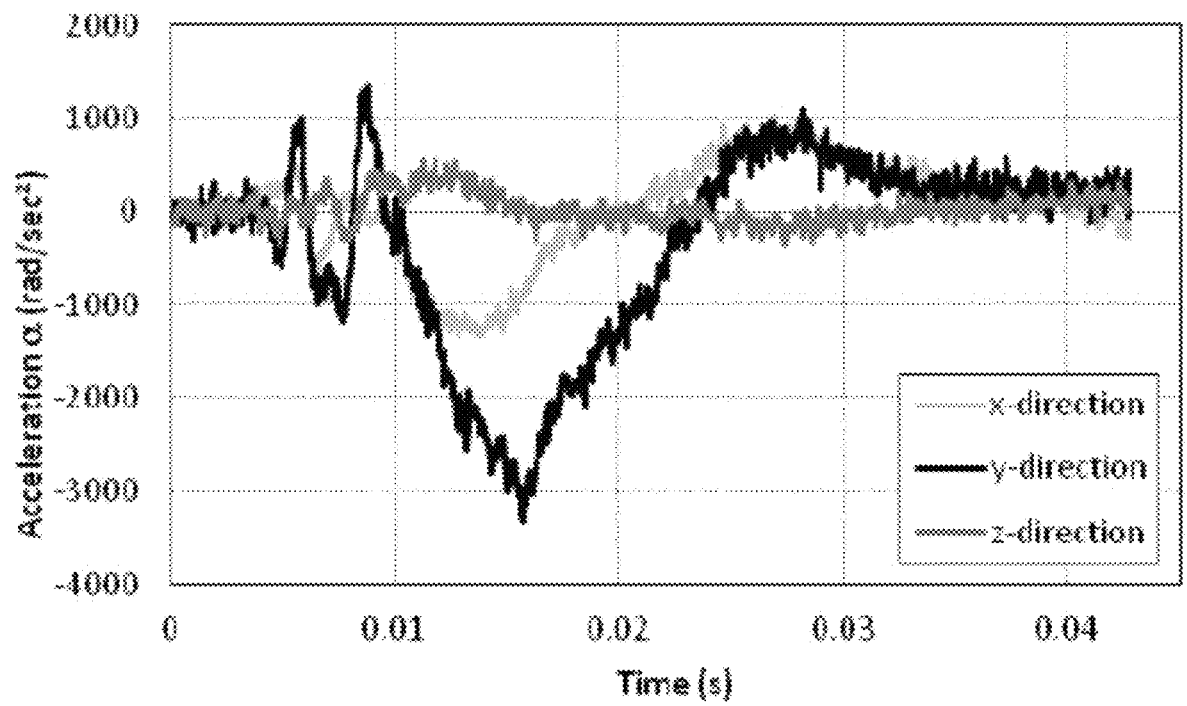
Figure 16:
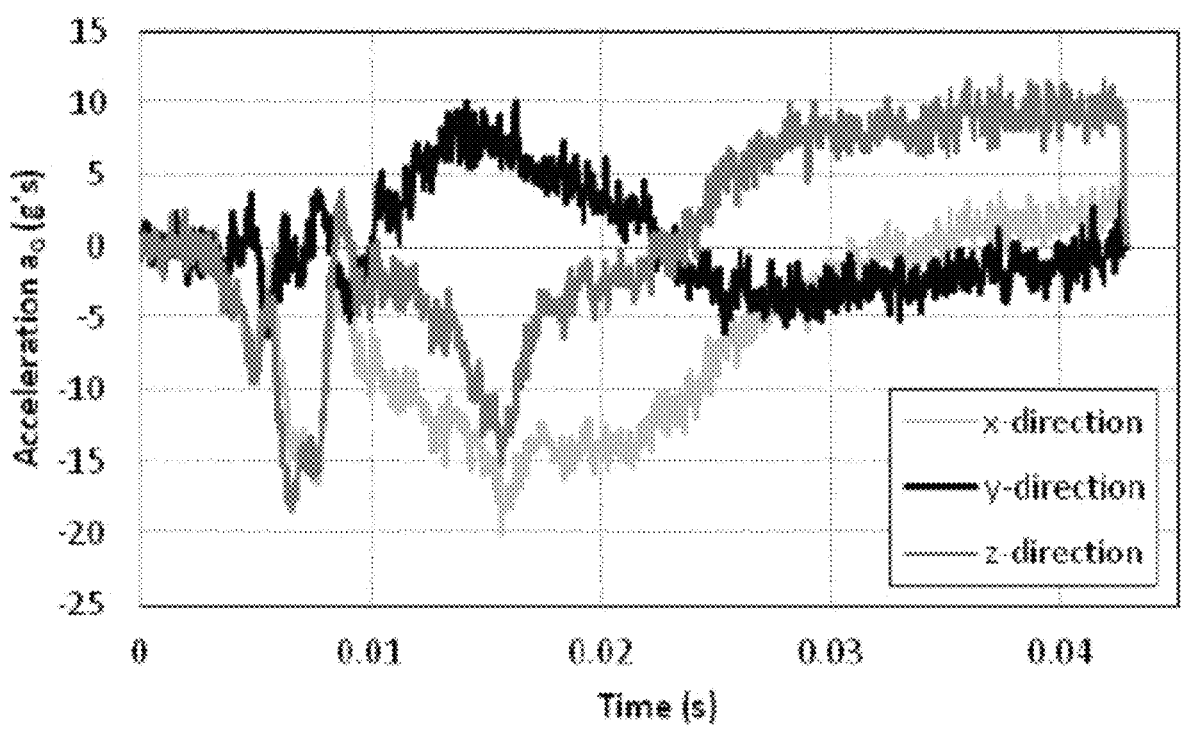
Figure 17:
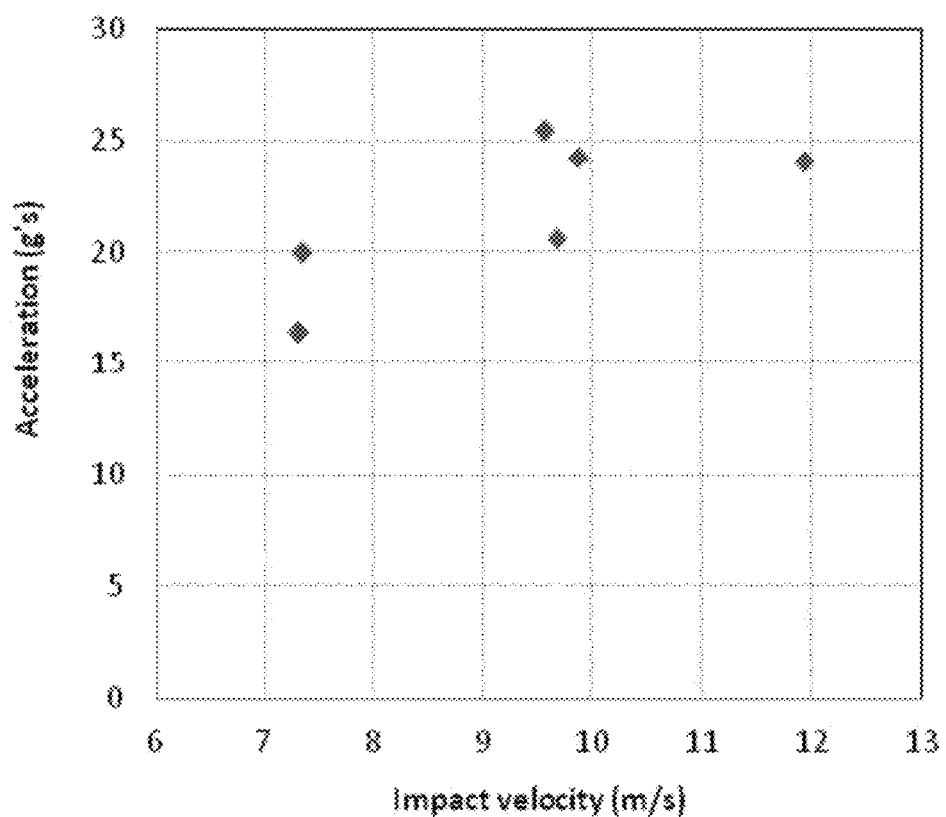

A total of six heading events were recorded using the technique described above. The headers were performed at a variety of speeds ranging up to approximately 12 m/s. The total delivered impulse is shown plotted as a function of initial ball velocity in FIG. 14. The linear accelerations measured by the left, right and center accelerometers (FIG. 11) were transformed to give the linear accelerations of the head CG in the x-, y- and z-directions, and the angular acceleration of the head about the x-, y- and z-axes, using rigid-body mechanics. For the header shown in FIG. 11, the angular accelerations of the head about the x-, y- and z-axes are shown in FIG. 15, and the linear accelerations of the head CG in the x-, y- and z-directions are shown in FIG. 16. The peak magnitude of the linear acceleration of the head CG in the sagittal plane is shown in FIG. 17 as a function of initial ball velocity. A linear acceleration of as high as 25 g's was observed for an initial ball velocity of 9.9 m/s.

Figure 18:
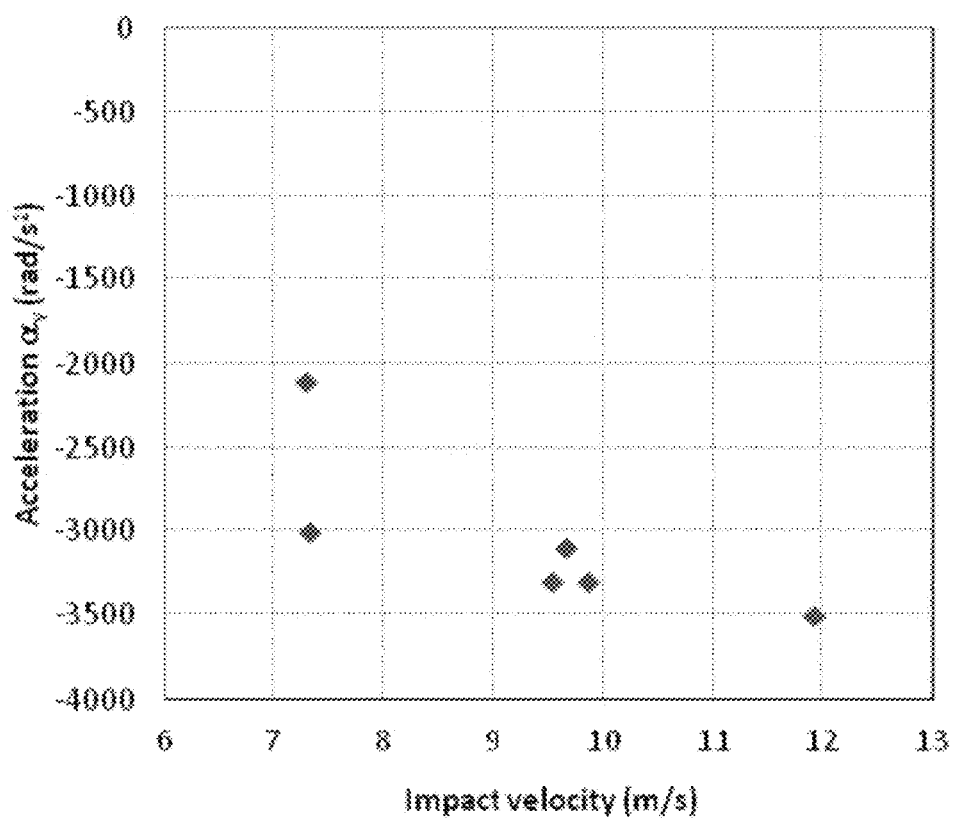

The peak angular accelerations of the head about the y-axis, $\alpha_y$, are shown in FIG. 18. An angular acceleration $\alpha_y$ having an absolute value of as high as 3500 rad/s$^2$ was observed for an initial ball velocity of 11.7 m/s. Angular velocities about the x- and z-axes, $\alpha_x$ and $\alpha_z$, were generally not appreciable for the headers recorded during this experiment, which focused on headers in which the impact between the soccer ball and the head is frontal and lies along the sagittal plane. It is not unheard of for soccer players to use other parts of the head to direct the motion of the ball. Thus, it is contemplated that a non-frontal header can result in appreciable angular accelerations about the x- and/or z-axes as well.

The data presented here supported a linear relationship between pre-impact ball velocity and delivered impulse, maximum linear acceleration of the head, and maximum angular acceleration of the head $\alpha_y$. The results demonstrated successful use of a custom mouth guard instrumented with three 3-axis accelerometers to determine both linear (CG) and angular accelerations of the head during soccer ball heading. It is expected that this instrumentation might be used in other situations where accelerations of the head are of interest.

Experimental Example Three

The following experimental example is further described in Birmingham et al., "An Instrumented Mouthguard to Measure Head Accelerations due to Impact," Proceedings of the ASME 2013 Summer Bioengineering Conference (SBC2013), June 26-29, Sunriver, Oreg., USA (2013), which is incorporated herein by reference in its entirety.

It is contemplated that, in the long term, quantitative measurements indicating the magnitude and nature of head impacts can be essential to understanding the biomechanics of head injury. Tools are needed that can quantitatively measure the levels of head acceleration experienced by athletes in a variety of situations in order to assess these risks. The disclosed experiment was aimed at developing instrumentation that is comfortable enough to use in the field and which can repeatably and accurately measure head accelerations from blows to the head. Soccer is a unique sport in that the unprotected head is deliberately used to direct the motion of the ball during play, which makes it practical to study in a controlled laboratory setting. While the possible long-term effects of heading are still subject to debate, there is evidence which suggests that it is responsible for transient neurocognitive deficits and transient concussion symptoms. The work presented here demonstrates the use of six 1-axis accelerometers, which make the mouthguard more slim and comfortable while allowing both linear and angular accelerations of the head to be determined.

The subject of this research was a 25-year-old male soccer player in good physical condition, with a height of 183 cm and a mass of 92 kg. A custom acrylic mouthguard, pictured in FIG. 23, was created from a mold of the subject's teeth and instrumented with six 1-axis microelectromechanical system (MEMS) accelerometers (Analog Devices, ADXL001), capable of measuring large accelerations with high acquisition rates (±70 g, 30 kHz), but of small enough mass to avoid significant inertial effects on the player's head.

The mouthguard was connected to a microcontroller, which wirelessly sent data to a data logger and laptop computer. During experimentation, a soccer ball launching machine (Sports Soccer Machine M1800, Jugs Sports Equipment) was used to launch balls at the test subject at speeds up to approximately 12 m/s. A standard size 5 soccer ball with diameter 22-23 cm, mass 0.43 kg, inflated to 62 kPa, was used. Experiments were performed indoors to eliminate wind. Each heading event was recorded using a high speed (HS) camera (HotShot 512 INT, NAC Image Technology) capable of recording up to 2,000 fps at its full resolution of 512×512 pixels. Contact between the ball and head typically lasts tens of milliseconds, allowing between 20 and 30 frames to be captured over the course of the impact. Frame-by-frame analysis of each video was performed using the Image Processing Toolbox available with MATLAB. The position of the ball was determined in each frame, as well as its geometric deformation during contact with the head. The pre- and post-impact velocities and the impulse delivered by the ball to the head were calculated from this information. The position of the head was tracked frame-by-frame just prior to impact, allowing the pre-impact head velocity to be determined. For lower initial ball velocities, where head velocity was appreciable, the relative impact speed between the ball and head was estimated by adding the incoming ball velocity with the pre-impact head velocity.

Figure 25:
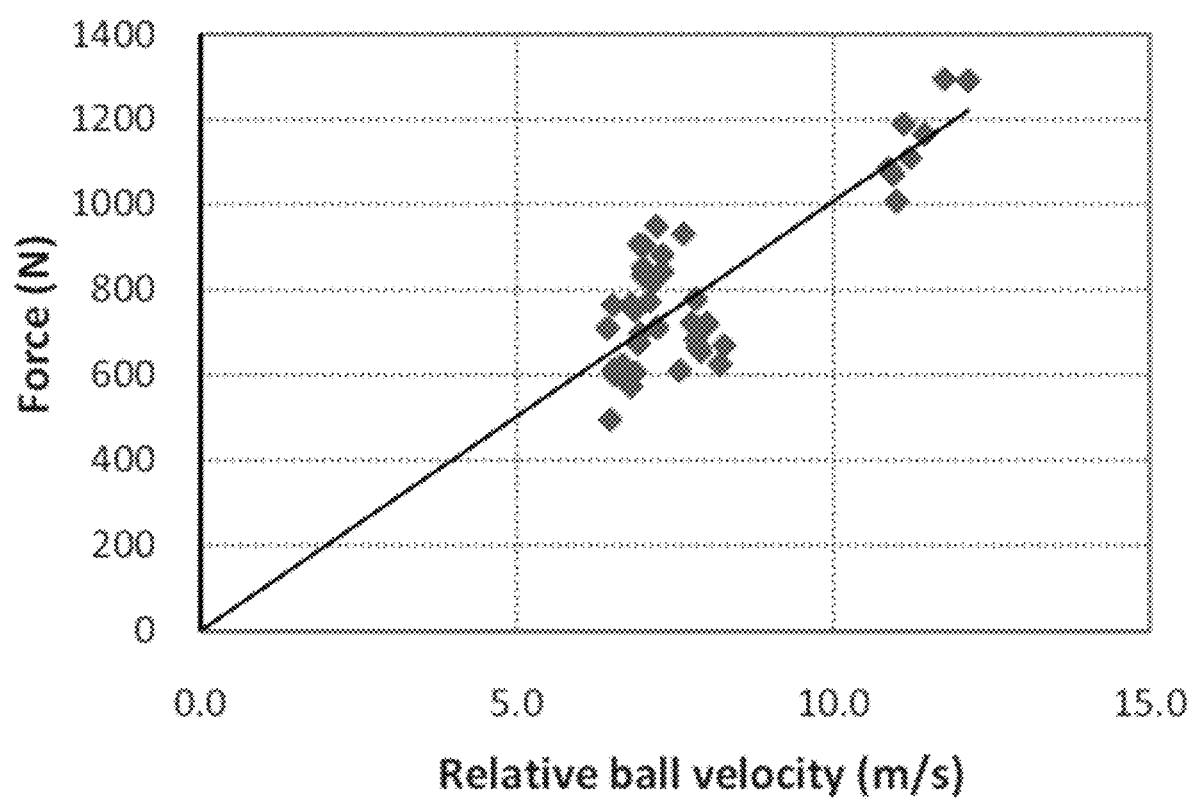
FIG. 25 depicts a graph of peak force of a ball on the head of a subject versus the relative ball velocity, as determined by high-speed-video frame-by-frame analysis as disclosed herein.

A total of forty-nine heading events were recorded using the technique described above, at incoming ball speeds between approximately 4 and 12 m/s. The peak force of the ball on the head as a function of relative impact velocity is shown in FIG. 25.

Figure 26:
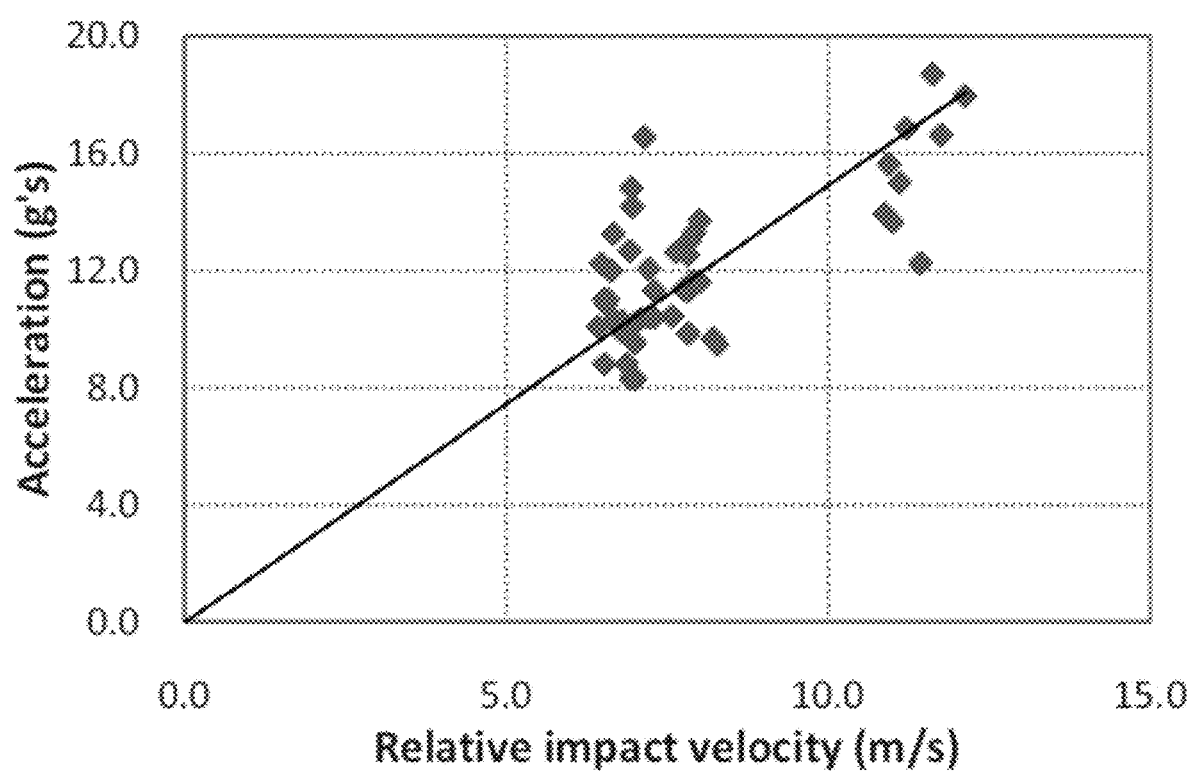
FIG. 26 depicts a graph of the peak magnitude of linear acceleration of the head center of mass of a subject in the saggital (xz) plane versus the relative ball velocity, as measured by an exemplary mouth guard as disclosed herein.
Figure 27:
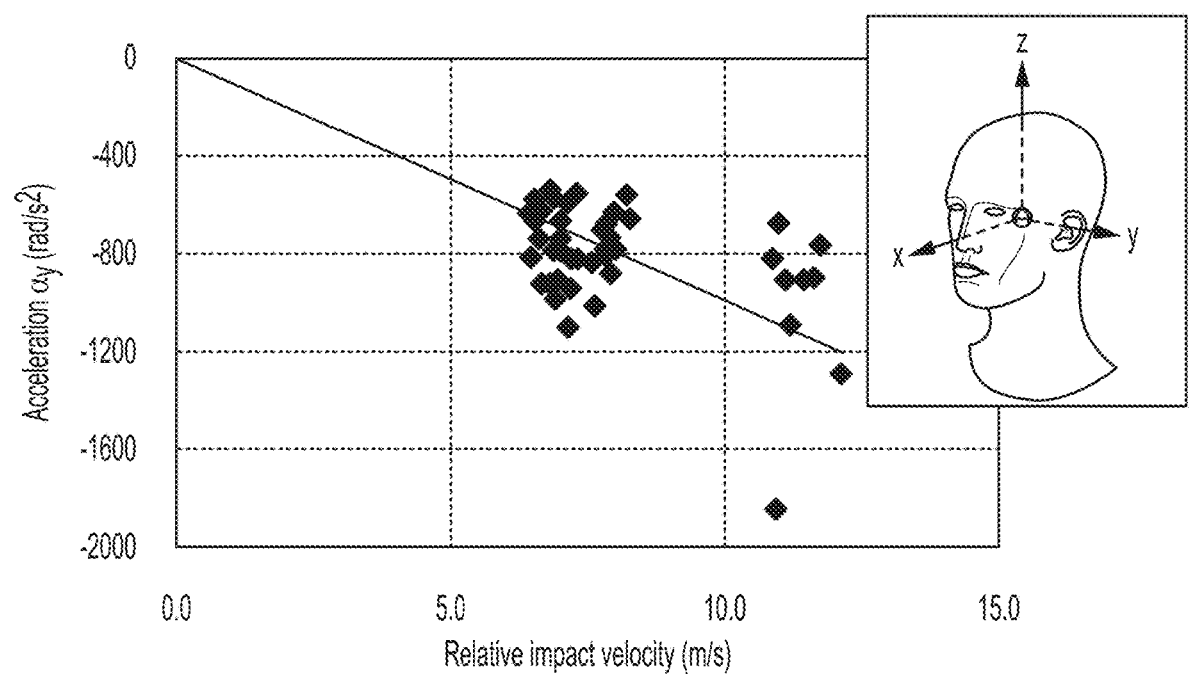
FIG. 27 depicts a graph of the angular acceleration of the head of a subject about the y-axis versus the relative ball velocity, as measured by an exemplary mouth guard as disclosed herein.

The linear accelerations measured by the left, right and center accelerometers were transformed to give the linear accelerations of the head CG in the x-, y- and z-directions, and the angular acceleration of the head about the x-, y- and z-axes, using rigid-body mechanics. The center of mass (CG) of the head is assumed to lie at the saggital plane, approximately beneath the zygomatic arch. The peak magnitude of the linear acceleration of the head CG in the saggital (xz) plane is shown in FIG. 26 as a function of relative ball velocity. The coordinate system used to describe the acceleration results is shown in the inset in FIG. 27. Linear acceleration ranged as high as 19 g's for a relative ball velocity of 11.6 m/s. The peak magnitude of the angular acceleration of the head about the y-axis, $\alpha_y$, is shown in FIG. 27. The absolute value of angular acceleration $\alpha_y$ ranged as high as 1852 rad/s$^2$ for a relative ball velocity of 10.9 m/s. Angular velocities about the x- and z-axes, $\alpha_x$ and $\alpha_z$, were generally not appreciable for the headers recorded during this experiment, which has focused on frontal headers.

The data presented here suggest a linear relationship between pre-impact velocity and delivered force, maximum linear acceleration of the head, and maximum angular acceleration of the head $\alpha_y$. The results presented here demonstrate successful use of a custom mouthguard instrumented with six 1-axis accelerometers to determine both linear (CG) and angular accelerations of the head during soccer ball heading.

Exemplary Aspects

In one exemplary aspect, a mouth guard for determining the linear and angular acceleration of the head of a subject is provided. The subject can have a head and upper and lower teeth. The mouth guard can comprise a U-shaped element having an outer side wall, an inner side wall, and at least one biting surface, the outer side wall, the inner side wall, and the at least one biting surface cooperating to define at least one channel configured to receive the upper teeth of the subject. The mouth guard can further comprise a plurality of accelerometers operatively associated with the U-shaped element, the plurality of accelerometers being spaced from one another about the U-shaped element, each accelerometer of the plurality of accelerometers being configured to produce an output indicative of the linear and angular acceleration of the mouth guard.

In another exemplary aspect, the plurality of accelerometers comprise at least one accelerometer positioned at a first location about the U-shaped element, at least one accelerometer positioned at a second location about the U-shaped element, and at least one accelerometer positioned at a third location about the U-shaped element, wherein the first, second, and third locations are spaced from one another about an arc defined by the U-shaped element.

In another exemplary aspect, the plurality of accelerometers comprise a first cluster of at least two accelerometers positioned at the first location, a second cluster of at least two accelerometers positioned at the second location, and a third cluster of at least two accelerometers positioned at the third location, and each accelerometer of the plurality of accelerometers is configured to measure linear acceleration in a single axis.

In another exemplary aspect, at least one accelerometer of the first, second, and third clusters is configured to measure linear acceleration in a first axis, at least one accelerometer of the first, second, and third clusters is configured to measure linear acceleration in a second axis, and the first axis is perpendicular to the second axis.

In another exemplary aspect, the plurality of accelerometers are substantially co-planar.

In another exemplary aspect, the mouth guard comprises first, second, and third receptacles coupled to the outer side wall of the mouth guard, the first receptacle is configured to receive the first cluster of accelerometers, the second receptacle is configured to receive the second cluster of accelerometers, and the third receptacle is configured to receive the third cluster of accelerometers.

In another exemplary aspect, the plurality of accelerometers comprise a first cluster of at least three accelerometers positioned at the first location, a second cluster of at least three accelerometers positioned at the second location, and a third cluster of at least three accelerometers positioned at the third location, and each accelerometer of the plurality of accelerometers is configured to measure linear acceleration in a single axis.

In another exemplary aspect, at least one accelerometer of the first, second, and third clusters is configured to measure linear acceleration in a first axis, at least one accelerometer of the first, second, and third clusters is configured to measure linear acceleration in a second axis, at least one accelerometer of the first, second, and third clusters is configured to measure linear acceleration in a third axis, and the first axis, the second axis, and the third axis are perpendicular to one another.

In another exemplary aspect, each accelerometer of the plurality of accelerometers is configured to measure linear acceleration in two-perpendicular axes.

In another exemplary aspect, each accelerometer of the plurality of accelerometers is configured to measure linear acceleration in three perpendicular axes.

In another exemplary aspect, the U-shaped element defines opposed first and second ends, the U-shaped element is substantially symmetrical about a central axis, the first location is proximate the first end of the U-shaped element, the second location is proximate the second end of the U-shaped element, and the central axis intersects the third location.

In one exemplary aspect, a system for determining the linear and angular acceleration of the head of a subject is provided. The system can comprise a mouth guard as disclosed herein and processing circuitry in operative communication with the plurality of accelerometers of the mouth guard. The processing circuitry can be configured to receive the outputs from the plurality of accelerometers.

In an additional exemplary aspect, a method of determining the linear and angular acceleration of the head of a subject is provided. The method can comprise positioning the head of the subject within a helmet, the helmet having a wall defining an inner chamber configured to receive the head of the subject, the helmet comprising a plurality of accelerometers operatively associated with the wall of helmet, the plurality of accelerometers being spaced from one another about the helmet. The method can further comprise positioning a mouth guard in engagement with the upper teeth of the subject, the mouth guard comprising a U-shaped element and a plurality of accelerometers operatively associated with the U-shaped element, the plurality of accelerometers being spaced from one another about the U-shaped element. The method can further comprise delivering a first impact force to the helmet, wherein, in response to delivery of the first impact force, each accelerometer of the plurality of accelerometers of the helmet is configured to produce an output indicative of the linear and angular acceleration of the helmet and each accelerometer of the plurality of accelerometers of the mouth guard is configured to produce an output indicative of the linear and angular acceleration of the mouth guard. The method can further comprise transmitting the outputs of the accelerometers of the helmet and the mouth guard to processing circuitry. The method can further comprise determining, through the processing circuitry, a transfer function configured to convert the outputs of the accelerometers of the helmet to the outputs of the accelerometers of the mouth guard. The method can further comprise disengaging the mouth guard from the teeth of the subject. The method can further comprise delivering a second impact force to the helmet, wherein, in response to delivery of the second impact force, each accelerometer of the plurality of accelerometers of the helmet is configured to produce an output indicative of the linear and angular acceleration of the helmet. The method can further comprise transmitting the outputs of the accelerometers of the helmet to the processing circuitry. The method can still further comprise applying, through the processing circuitry, the transfer function to the outputs of the accelerometers of the helmet to determine the linear and angular acceleration of the head of the subject.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A mouth guard for determining linear acceleration of a head of a subject, the subject having upper and lower teeth, the mouth guard having an x-y-z coordinate system with orthogonal x, y, and z axes, the mouth guard comprising:
a U-shaped element having an outer side wall, an inner side wall, and at least one biting surface, the outer side wall, the inner side wall, and the at least one biting surface cooperating to define at least one channel configured to receive the upper teeth of the subject; and
a plurality of clusters of accelerometers operatively associated with the U-shaped element, the plurality of clusters of accelerometers being spaced from one another about the U-shaped element, each accelerometer of the plurality of clusters of accelerometers being configured to produce an output indicative of linear acceleration of the mouth guard,
wherein the plurality of clusters of accelerometers comprise a first cluster positioned at a first location about the U-shaped element, a second cluster positioned at a second location about the U-shaped element, and a third cluster positioned at a third location about the U-shaped element, wherein the first, second, and third locations are spaced from one another about an arc defined by the U-shaped element, wherein the accelerometers of the plurality of clusters are co-planar with an x-y plane defined by the x and y axes, and wherein each of the first, second, and third clusters of accelerometers consists of two accelerometers,
wherein the U-shaped element defines opposed first and second ends, wherein the U-shaped element and the plurality of clusters of accelerometers are substantially symmetrical about an x-z plane defined by the x and z axes, the x-z plane containing a central axis, wherein the first location is proximate the first end of the U-shaped element, wherein the second location is proximate the second end of the U-shaped element, and wherein the central axis intersects the third location.

2. The mouth guard of claim 1, wherein each accelerometer of the plurality of accelerometers is configured to measure linear acceleration in a single axis.

3. The mouth guard of claim 2, wherein at least one accelerometer of the first, second, and third clusters is configured to measure linear acceleration in a first axis, wherein at least one accelerometer of the first, second, and third clusters is configured to measure linear acceleration in a second axis, wherein the first axis is perpendicular to the second axis.

4. The mouth guard of claim 1, wherein the mouth guard comprises first, second, and third receptacles coupled to the outer side wall of the mouth guard, wherein the first receptacle is configured to receive the first cluster of accelerometers, wherein the second receptacle is configured to receive the second cluster of accelerometers, and wherein the third receptacle is configured to receive the third cluster of accelerometers.

5. A system for determining linear and angular acceleration of a head of a subject, the subject having upper and lower teeth, the system comprising:
a mouth guard having an x-y-z coordinate system with orthogonal x, y, and z axes, the mouth guard comprising:
a U-shaped element having an outer side wall, an inner side wall, and at least one biting surface, the outer side wall, the inner side wall, and the at least one biting surface cooperating to define at least one channel configured to receive the upper teeth of the subject; and
a plurality of clusters of accelerometers operatively associated with the U-shaped element, the plurality of clusters of accelerometers being spaced from one another about the U-shaped element, each accelerometer of the plurality of clusters of accelerometers being configured to produce an output indicative of linear acceleration of the mouth guard,
wherein the plurality of clusters of accelerometers comprise a first cluster positioned at a first location about the U-shaped element, a second cluster positioned at a second location about the U-shaped element, and a third cluster positioned at a third location about the U-shaped element, wherein the first, second, and third locations are spaced from one another about an arc defined by the U-shaped element, and wherein the accelerometers of the plurality of clusters positioned at the first, second, and third locations are co-planar with an x-y plane defined by the x and y axes, and wherein each of the first, second, and third clusters of accelerometers consists of two accelerometers,
wherein the U-shaped element defines opposed first and second ends, wherein the U-shaped element and plurality of clusters of accelerometers are substantially symmetrical about an x-z plane defined by the x and z axes, the x-z plane containing a central axis, wherein the first location is proximate the first end of the U-shaped element, wherein the second location is proximate the second end of the U-shaped element, and wherein the central axis intersects the third location; and
processing circuitry in operative communication with the plurality of accelerometers of the mouth guard, wherein the processing circuitry is configured to receive the outputs from the plurality of accelerometers.

6. The system of claim 5, wherein each accelerometer of the plurality of accelerometers is configured to measure linear acceleration in a single axis.

7. The system of claim 6, wherein at least one accelerometer of the first, second, and third clusters is configured to measure linear acceleration in a first axis, wherein at least one accelerometer of the first, second, and third clusters is configured to measure linear acceleration in a second axis, and wherein the first and second axes are perpendicular to one another.

8. The system of claim 7, wherein the mouth guard comprises first, second, and third receptacles coupled to the outer side wall of the mouth guard, wherein the first receptacle is configured to receive the first cluster of accelerometers, wherein the second receptacle is configured to receive the second cluster of accelerometers, and wherein the third receptacle is configured to receive the third cluster of accelerometers.

* * * * *